United States Patent
Akmal et al.

(10) Patent No.: US 12,146,779 B2
(45) Date of Patent: Nov. 19, 2024

(54) METHOD AND SYSTEM FOR SEPARATING AND ANALYZING MULTIPHASE IMMISCIBLE FLUID MIXTURES

(71) Applicant: Saudi Arabian Oil Company, Dhahran (SA)

(72) Inventors: Naim Akmal, Dhahran (SA); Hossam Qusty, Dhahran (SA); Saleh Sharidi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 486 days.

(21) Appl. No.: 17/482,150

(22) Filed: Sep. 22, 2021

(65) Prior Publication Data

US 2023/0093403 A1 Mar. 23, 2023

(51) Int. Cl.
*G01F 1/74* (2006.01)
*E21B 43/34* (2006.01)
(Continued)

(52) U.S. Cl.
CPC .............. *G01F 1/74* (2013.01); *E21B 43/34* (2013.01); *E21B 49/088* (2013.01); *G01F 15/08* (2013.01);
(Continued)

(58) Field of Classification Search
CPC .......... G01F 1/74; G01F 15/08; G01F 15/005; G01F 23/0007; E21B 43/34;
(Continued)

(56) References Cited

U.S. PATENT DOCUMENTS

| 3,712,118 A | 1/1973 | Mason et al. |
| 4,481,130 A | 11/1984 | Robertson |

(Continued)

FOREIGN PATENT DOCUMENTS

| CN | 101670197 B | 12/2011 |
| CN | 102128658 B | 7/2012 |

(Continued)

OTHER PUBLICATIONS

Rodriguez et al., "Treatment of Produced Water In the Permian Basin For Hydraulic Fracturing: Comparison of Different Coagulation Processes and Innovative Filter Media", MDPI Water, 12, 770, Mar. 11, 2020, pp. 1-16.

(Continued)

*Primary Examiner* — Peter J Macchiarolo
*Assistant Examiner* — Anthony W Megna Fuentes
(74) *Attorney, Agent, or Firm* — Bracewell LLP; Constance G. Rhebergen; Keith R. Derrington

(57) ABSTRACT

A first aqueous liquid phase sample is drawn from a first one of a plurality of separation vessels in response to determining that a first separation operation in the first separation vessel has completed. First aqueous liquid phase sample data is obtained by analyzing the first aqueous liquid phase sample with at least one sensor. A sample of a second aqueous liquid phase is drawn from a second one of the plurality of separation vessels in response to determining that a second separation operation in the second separation vessel has completed. Second aqueous liquid phase sample data is obtained by analyzing the second aqueous liquid phase sample with the at least one sensor. The second aqueous liquid phase sample data is transmitted to the external multiphase flow meter. The first separation operation in the first separation vessel and the second separation operation in the second separation vessel are concurrent.

23 Claims, 3 Drawing Sheets

(51) Int. Cl.
| | |
|---|---|
| *E21B 49/08* | (2006.01) |
| *G01F 15/08* | (2006.01) |
| *G01N 1/10* | (2006.01) |
| *G01N 1/38* | (2006.01) |
| *G01N 33/18* | (2006.01) |
| *B01D 21/00* | (2006.01) |
| *G01F 15/00* | (2006.01) |
| *G01F 23/00* | (2022.01) |
| *G01N 1/40* | (2006.01) |

(52) U.S. Cl.
CPC ............... *G01N 1/10* (2013.01); *G01N 1/38* (2013.01); *G01N 33/18* (2013.01)

(58) Field of Classification Search
CPC .......... E21B 49/088; G01N 1/10; G01N 1/38; G01N 33/18; G01N 33/1886; G01N 33/1893; G01N 1/4044; B01D 21/00
See application file for complete search history.

(56) References Cited

U.S. PATENT DOCUMENTS

| | | | |
|---|---|---|---|
| 4,581,134 A | 4/1986 | Richter, Jr. et al. | |
| 5,078,856 A | 1/1992 | Yamaguchi et al. | |
| 5,637,201 A | 6/1997 | Raguse et al. | |
| 5,741,409 A | 4/1998 | Raguse et al. | |
| 5,753,093 A | 5/1998 | Raguse et al. | |
| 6,004,442 A | 12/1999 | Choulga et al. | |
| 6,872,239 B2 | 3/2005 | Nilsen et al. | |
| 7,140,441 B2 | 11/2006 | Hauge et al. | |
| 7,147,788 B2 | 12/2006 | Tveiten | |
| 7,231,819 B2 | 6/2007 | Jones et al. | |
| 7,373,813 B2 | 5/2008 | Difoggio | |
| 7,474,969 B2 | 1/2009 | Poulisse | |
| 7,661,302 B2 | 2/2010 | Gysling | |
| 7,775,085 B2 | 8/2010 | Scott | |
| 7,966,892 B1 | 6/2011 | Halilah | |
| 8,177,958 B2 | 5/2012 | Lawrence et al. | |
| 8,720,573 B2 | 5/2014 | Eriksen | |
| 8,790,509 B2 | 7/2014 | Vu | |
| 8,935,100 B2 | 1/2015 | Weiner et al. | |
| 9,052,285 B2 | 6/2015 | Muller et al. | |
| 9,239,406 B2 | 1/2016 | Kalia et al. | |
| 9,284,705 B2 | 3/2016 | Theegala | |
| 9,314,715 B2 | 4/2016 | Grave et al. | |
| 9,341,058 B2 | 5/2016 | Keizer et al. | |
| 9,540,574 B2 | 1/2017 | Janssen et al. | |
| 9,658,178 B2 | 5/2017 | Surman et al. | |
| 9,696,193 B2 | 7/2017 | Martin et al. | |
| 9,840,895 B1 | 12/2017 | Kuhn | |
| 9,863,926 B2 | 1/2018 | Kriel et al. | |
| 10,023,811 B2 | 7/2018 | Soliman et al. | |
| 10,260,010 B2 | 4/2019 | Soliman | |
| 10,350,515 B2 | 7/2019 | Al-Shafei et al. | |
| 10,597,313 B2 | 3/2020 | Raynel et al. | |
| 2005/0269072 A1 | 12/2005 | Folk et al. | |
| 2010/0200221 A1 | 8/2010 | Sipos | |
| 2012/0111571 A1 | 5/2012 | Eriksen | |
| 2013/0026082 A1 | 1/2013 | Al-Shafei et al. | |
| 2016/0052799 A1 | 2/2016 | Grave et al. | |
| 2017/0319984 A1 | 11/2017 | Oshinowo | |
| 2018/0244539 A1 | 8/2018 | Asdahl et al. | |
| 2018/0299423 A1 | 10/2018 | Leblanc | |
| 2019/0010796 A1 | 1/2019 | De Freitas et al. | |
| 2019/0049425 A1 | 2/2019 | Marshall et al. | |
| 2019/0211274 A1 | 7/2019 | Soliman et al. | |
| 2020/0102234 A1 | 4/2020 | Patton | |
| 2020/0255748 A1 | 8/2020 | Soliman et al. | |
| 2021/0102831 A1 | 4/2021 | Ahmad et al. | |
| 2022/0380688 A1 | 12/2022 | Soliman | |
| 2023/0086247 A1 | 3/2023 | Akmal et al. | |
| 2023/0089200 A1 | 3/2023 | Akmal et al. | |
| 2023/0093403 A1 | 3/2023 | Akmal et al. | |

FOREIGN PATENT DOCUMENTS

| | | | | |
|---|---|---|---|---|
| CN | 112593925 A | * | 4/2021 | ............ E21B 43/34 |
| WO | 2001074468 A3 | | 10/2001 | |
| WO | 2021043923 A1 | | 3/2021 | |
| WO | WO-2021086401 A1 | * | 5/2021 | ............... G01F 1/74 |

OTHER PUBLICATIONS

Ghorbani et al., "Validating Automated Real-Time Produced Water Composition Measurement Device With Field Produced Water Samples: A Pathway to Filed Trial", SPE-188244-MS, Nov. 13, 2017, 2 pages.

Hach, "Complete Water Analysis For The Upstream Oil & Gas Industry", 2014, 20 pages.

Hansen et al., "Multi-Phase Flow Metering In Offshore Oil and Gas Transportation Pipelines: Trends and Perspectives", WWW.mdpi.com/journal/sensors, 19, 2184, May 11, 2019, pp. 1-26.

Roach et al., "A Multiphase Flow Meter For the On-Line Determination of the Flow Rates of Oil, Water and Gas", AU9817323, 1997, CSIRO Minerals, pp. 106-111.

Andreussi, P. et al.; "Application of a wet gas meter to detect extremely low liquid volume fractions" BHR Group 2007 Multiphase Production Technology 13; pp. 297-308.

SA Substantive Examination Report Notification dated Sep. 2, 2024 for SA Application No. 122440155.

* cited by examiner

METHOD AND SYSTEM FOR SEPARATING AND ANALYZING MULTIPHASE IMMISCIBLE FLUID MIXTURES

TECHNICAL FIELD

Embodiments of the present disclosure relate generally to a method and system for separating and analyzing samples obtained from multiphase immiscible fluid mixtures. In particular, embodiments of the present disclosure relate to utilizing multiple separation chambers to increase sample measurement rate.

BACKGROUND

Multiphase immiscible fluid mixtures (e.g., multiphase fluids) produced from oil wells typically are a mixture of gas, liquid hydrocarbons, and salty formation water (e.g., produced water). For example, an oil well may produce polar and nonpolar molecules along with gases such as carbon dioxide, hydrogen sulfide, carbon disulfide, and the like. A gas oil separation plant (GOSP) is used in the upstream oil and gas industry to refer to temporary or permanent facilities that separate the multiphase immiscible fluid mixtures from a plurality of wells (e.g., more than a hundred oil wells) into constituent vapor and liquid components (e.g., liquid hydrocarbons, and salty formation or produced water) and generate dry crude oil that meets predetermined customer specifications. A typical GOSP includes a high pressure production trap (HPPT), a low pressure production trap (LPPT), a low pressure degassing tank (LPDT), a dehydrator unit, first and second stage desalting units, a water/oil separation plant (WOSEP), a stabilizer column, centrifugal pumps, heat exchangers, and reboilers.

Composition of the multiphase immiscible fluid mixture produced from each well feeding into the GOSP typically varies over time. Generally, a greater amount of crude oil is produced initially from the well. Over time, the amount of produced water increases and the amount of crude oil produced decreases. It is necessary to know the amount of crude oil and produced water produced from each well of the GOSP in order to manage the production of each well, while maintaining overall efficiency of the GOSP and generating dry crude oil that meets the predetermined customer specifications. For example, if a particular well is producing a high proportion of water, it may be desirable to isolate the well from the flow of the GOSP.

A multiphase flow meter (MPFM) may be used at the GOSP (or at a well site) to measure the amount of crude oil and produced water produced from each well. The MPFM's built-in software and algorithm can be utilized to determine the flow of oil from the combined flow of produced water and crude oil. To obtain accurate measurement of amount or flow rate of crude oil and produced water passing through the MPFM, it is necessary to calibrate the MPFM using data regarding certain physical or chemical properties of the produced water passing through. That is, it is necessary to enter certain properties of the produced water into the MPFM panel so that the flow meter displays information regarding the flow of oil (and of the water) with a low margin of error. To perform such calibration, conventionally, a sample of the multiphase immiscible fluid mixture (from one well or a group of wells) is collected in a test trap. The test trap can be rated as having high pressure, intermediate pressure, or low pressure. Crude oil in the sample is allowed to separate from produced water in the test trap, and a portion of the separated produced water is collected and sent to a local laboratory to analyze certain geophysical properties (e.g., salinity, chloride content, conductivity, and the like) of the separated produced water. The data obtained by this analysis is used to calibrate the MPFM. More specifically, the analytical results received from the laboratory are manually fed into the MPFM panel to optimize or calibrate the oil and water flow rate data coming out of the MPFM. Thus, the analytical data entered in the MPFM enables the MPFM to accurately calculate the amount of water present in the oil water immiscible fluid mixture passing therethrough.

The act of collection of the produced water sample, transferring the sample to the laboratory, and measuring the geophysical properties of the sample can take approximately two to three days. Further, the analytical data received from the laboratory must be manually fed into the MPFM, thereby creating the possibility of introducing a data entry error. Still further, the above process must be repeated for each sample of each well feeding into the GOSP to accurately measure the flow rates of each phase of the multiphase immiscible fluid mixture produced from each well, to thereby provide the GOSP with all of the information necessary for the control and optimization of the overall flow from the oil field or the GOSP. A better and more automated approach that is less prone to human error is desirable.

SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the disclosed subject matter or to delineate the scope of the disclosed subject matter. Its sole purpose is to present some concepts in a simplified form as a prelude to the more detailed description that is discussed later.

In one embodiment, system for separating and analyzing multiphase fluids includes: a plurality of separation vessels; a water analysis unit in fluid communication with each of the plurality of separation vessels, the water analysis unit including at least one sensor; and one or more processors operatively coupled to at least the sensor, the one or more processors configured to: draw a sample of a first aqueous liquid phase from a first one of the plurality of separation vessels in response to determining that a first separation operation in the first separation vessel has completed; obtain first aqueous liquid phase sample data by analyzing the first aqueous liquid phase sample with the at least one sensor in the water analysis unit; transmit the first aqueous liquid phase sample data to an external multiphase flow meter; draw a sample of a second aqueous liquid phase from a second one of the plurality of separation vessels in response to determining that a second separation operation in the second separation vessel has completed; obtain second aqueous liquid phase sample data by analyzing the second aqueous liquid phase sample with the at least one sensor in the water analysis unit; and transmit the second aqueous liquid phase sample data to the multiphase flow meter, where the first separation operation in the first separation vessel and the second separation operation in the second separation vessel are concurrent.

In another embodiment, the first separation operation is determined to be complete by the one or more processors when a first discrete sample of multiphase fluid contained in the first separation vessel has separated into liquid phases including the first aqueous liquid phase and a first nonpolar liquid phase, and the wherein the second separation operation is determined to be complete by the one or more processors when a second discrete sample of multiphase fluid contained in the second separation vessel has separated into liquid phases including the second aqueous liquid phase and a second nonpolar liquid phase.

In yet another embodiment, each of the plurality of separation vessels includes a multiphase fluid inlet, a demulsifier inlet, and at least one level sensor, and where the one or more processors are further operatively coupled to each level sensor, and are further configured to: introduce the first discrete sample of multiphase fluid into the first separation vessel via the multiphase fluid inlet thereof based on sensor data from the level sensor thereof; add a predetermined amount and type of demulsifier from a demulsifier source into the first separation vessel containing the first discrete sample of multiphase fluid via the demulsifier inlet thereof, wherein the first separation operation starts when the predetermined amount and type of demulsifier is added to the first separation vessel; introduce the second discrete sample of multiphase fluid into the second separation vessel via the multiphase fluid inlet thereof based on sensor data from the level sensor thereof; and add a predetermined amount and type of demulsifier from the demulsifier source into the second separation vessel containing the second discrete sample of multiphase fluid via the demulsifier inlet thereof, wherein the second separation operation starts when the predetermined amount and type of demulsifier is added to the second separation vessel.

In yet another embodiment, the one or more processors are further configured to: determine that the first separation operation is complete when a first predetermined period of time has elapsed since start of the first separation operation; and determine that the second separation operation is complete when a second predetermined period of time has elapsed since start of the second separation operation.

In yet another embodiment, the one or more processors are further configured to: determine the predetermined amount and type of demulsifier to be added to the first separation vessel based on at least one of a type of crude oil and an amount of produced water that is typically produced from the first discrete sample of multiphase fluid; and determine the predetermined amount and type of demulsifier to be added into the second separation vessel based on at least one of a type of crude oil and an amount of produced water that is typically produced from the second discrete sample of multiphase fluid.

In yet another embodiment, the system further includes: a plurality of gas flow lines that are in fluid communication with the plurality of separation vessels, respectively; and a plurality of flow meters respectively disposed on the plurality of gas flow lines and operatively coupled to the one or more processors, and where, for each separation vessel: the gas flow line vents a gas phase of the multiphase fluid contained therein, and one or more processors are further configured to control the flow meter to obtain measurement data of an amount of gas exiting the separation vessel.

In yet another embodiment, the one or more processors are further configured to: dilute the first aqueous liquid phase sample drawn from the first separation vessel with a predetermined amount of fresh water from a fresh water source to generate a first diluted aqueous liquid phase sample; measure first diluted aqueous liquid phase sample data by analyzing the first diluted aqueous liquid phase sample with the at least one sensor in the water analysis unit; obtain the first aqueous liquid phase sample data based on the measured first diluted aqueous liquid phase sample data and by accounting for the predetermined amount of fresh water; dilute the second aqueous liquid phase sample drawn from the second separation vessel with the predetermined amount of fresh water to generate a second diluted aqueous liquid phase sample; measure second diluted aqueous liquid phase sample data by analyzing the second diluted aqueous liquid phase sample with the at least one sensor in the water analysis unit; and obtain the second aqueous liquid phase sample data based on the measured second diluted aqueous liquid phase sample data and by accounting for the predetermined amount of fresh water.

In yet another embodiment, the one or more processors are further configured to: drain the first diluted aqueous liquid phase sample from the water analysis unit; rinse one or more flow cells of the water analysis unit with fresh water; and introduce the second diluted aqueous liquid phase sample in the water analysis unit to measure the second diluted aqueous liquid phase sample data after rinsing the one or more flow cells of the water analysis unit.

In yet another embodiment, the one or more processors are further configured to: maintain the first diluted aqueous liquid phase sample in predetermined contact with the at least one sensor in the water analysis unit until an output from the at least one sensor has stabilized; and measure the first diluted aqueous liquid phase sample data in response to determining that the output from the at least one sensor has stabilized.

In yet another embodiment, the one or more processors are further configured to determine that the output from the at least one sensor has stabilized based on passage of a predetermined period of time since start of the predetermined contact of the first diluted aqueous liquid phase sample with the at least one sensor in the water analysis unit.

In yet another embodiment, the one or more processors configured to draw the first aqueous liquid phase sample from the first separation vessel comprises the one or more processors configured to control a first sample control valve and a pump assembly to draw a predetermined amount of the first aqueous liquid phase from the first separation vessel as the first aqueous liquid phase sample, where the one or more processors configured to draw the second aqueous liquid phase sample from the second separation vessel comprises the one or more processors configured to control a second sample control valve and the pump assembly to draw a predetermined amount of the second aqueous liquid phase from the second separation vessel as the second aqueous liquid phase sample, and where the one or more processors configured to dilute each of the first and second aqueous liquid phase samples with the predetermined amount of fresh water comprises the one or more processors configured to control a fresh water control valve and the pump assembly to draw the predetermined amount of fresh water from the fresh water source.

In yet another embodiment, the at least one sensor includes a plurality of sensors to measure a plurality of properties of the first and second aqueous liquid phase samples, and wherein the plurality of sensors are selected from a group of sensors including a total dissolved solids (TDS) sensor, a salinity sensor, a pH sensor, a conductivity sensor, a sodium concentration sensor, a chloride concentration sensor, a sulfate concentration sensor, a carbonate concentration sensor, and a nitrate concentration sensor. In yet another embodiment, each sensor has a sensing area that is covered with a layer of an ion-exchange polymer and that is adapted to remain in predetermined contact with an aqueous liquid phase sample during the analysis.

In yet another embodiment, a method for separating and analyzing multiphase fluids includes: drawing a sample of a first aqueous liquid phase from a first one of a plurality of separation vessels in response to determining that a first separation operation in the first separation vessel has completed; obtaining first aqueous liquid phase sample data by analyzing the first aqueous liquid phase sample with at least one sensor; transmitting the first aqueous liquid phase sample data to an external multiphase flow meter; drawing a sample of a second aqueous liquid phase from a second one of the plurality of separation vessels in response to determining that a second separation operation in the second separation vessel has completed; obtaining second aqueous liquid phase sample data by analyzing the second aqueous liquid phase sample with the at least one sensor; and transmitting the second aqueous liquid phase sample data to the multiphase flow meter, where the first separation operation in the first separation vessel and the second separation operation in the second separation vessel are concurrent.

In yet another embodiment, the first separation operation is complete when a first discrete sample of multiphase fluid contained in the first separation vessel has separated into liquid phases including the first aqueous liquid phase and a first nonpolar liquid phase, and the wherein the second separation operation is complete when a second discrete sample of multiphase fluid contained in the second separation vessel has separated into liquid phases including the second aqueous liquid phase and a second nonpolar liquid phase.

In yet another embodiment, each of the plurality of separation vessels includes a multiphase fluid inlet, a demulsifier inlet, and at least one level sensor, and where the method further includes: introducing the first discrete sample of multiphase fluid into the first separation vessel via the multiphase fluid inlet thereof, based on sensor data from the level sensor thereof; adding a predetermined amount and type of demulsifier from a demulsifier source into the first separation vessel containing the first discrete sample of multiphase fluid via the demulsifier inlet thereof, wherein the first separation operation starts when the predetermined amount and type of demulsifier is added to the first separation vessel; introducing the second discrete sample of multiphase fluid into the second separation vessel via the multiphase fluid inlet thereof, based on sensor data from the level sensor thereof; and adding a predetermined amount and type of demulsifier from the demulsifier source into the second separation vessel containing the second discrete sample of multiphase fluid via the demulsifier inlet thereof, wherein the second separation operation starts when the predetermined amount and type of demulsifier is added to the second separation vessel.

In yet another embodiment, the method further includes: determining that the first separation operation is complete when a first predetermined period of time has elapsed since start of the first separation operation; and determining that the second separation operation is complete when a second predetermined period of time has elapsed since start of the second separation operation. In yet another embodiment, the method further includes: determining the predetermined amount and type of demulsifier to be added into the first separation vessel based on at least one of a type of crude oil and an amount of produced water that is typically produced from the first discrete sample of multiphase fluid; and determining the predetermined amount and type of demulsifier to be added into the second separation vessel based on at least one of a type of crude oil and an amount of produced water that is typically produced from the second discrete sample of multiphase fluid.

In yet another embodiment, the method further includes: diluting the first aqueous liquid phase sample drawn from the first separation vessel with a predetermined amount of fresh water to generate a first diluted aqueous liquid phase sample; measuring first diluted aqueous liquid phase sample data by analyzing the first diluted aqueous liquid phase sample with the at least one sensor; obtaining the first aqueous liquid phase sample data based on the measured first diluted aqueous liquid phase sample data and by accounting for the predetermined amount of fresh water; diluting the second aqueous liquid phase sample drawn from the second separation vessel with the predetermined amount of fresh water to generate a second diluted aqueous liquid phase sample; measuring second diluted aqueous liquid phase sample data by analyzing the second diluted aqueous liquid phase sample with the at least one sensor; and obtaining the second aqueous liquid phase sample data based on the measured second diluted aqueous liquid phase sample data and by accounting for the predetermined amount of fresh water.

In yet another embodiment, the method further includes: draining the first diluted aqueous liquid phase sample; rinsing a flow cell corresponding to the at least one sensor with fresh water; and introducing the second diluted aqueous liquid phase sample to the flow cell to measure the second diluted aqueous liquid phase sample data after the rinsing. In yet another embodiment, the method further includes: maintaining the first diluted aqueous liquid phase sample in predetermined contact with the at least one sensor until an output from the at least one sensor has stabilized; and measuring the first diluted aqueous liquid phase sample data in response to determining that the output from the at least one sensor has stabilized; and determining that the output from the at least one sensor has stabilized based on passage of a predetermined period of time since start of the predetermined contact of the first diluted aqueous liquid phase sample with the at least one sensor.

In yet another embodiment, the step of drawing the first aqueous liquid phase sample from the first separation vessel comprises controlling a first sample control valve and a pump assembly to draw a predetermined amount of the separated first aqueous liquid phase from the first separation vessel as the first aqueous liquid phase sample, the step of drawing the second aqueous liquid phase sample from the second separation vessel comprises controlling a second sample control valve and the pump assembly to draw a predetermined amount of the separated second aqueous liquid phase from the second separation vessel as the second aqueous liquid phase sample, and the steps of diluting each of the first and second aqueous liquid phase samples with the predetermined amount of fresh water comprise controlling a fresh water control valve and the pump assembly to add the predetermined amount of fresh water to a respective aqueous liquid phase sample.

In yet another embodiment, a system for separating and analyzing multiphase fluids includes: a plurality of separation vessels, each separation vessel including: an inner chamber that is adapted to contain a discrete sample of multiphase fluid; a multiphase fluid inlet to introduce the discrete sample of multiphase fluid into the separation vessel; at least one level sensor to detect a level of the multiphase fluid inside the inner chamber; a demulsifier inlet to introduce a predetermined amount and type of demulsifier into the inner chamber to mix with the discrete sample of multiphase fluid, wherein introduction of the demulsifier into the inner chamber starts a separation operation to separate the discrete sample of multiphase fluid into liquid phases including an aqueous liquid phase and a nonpolar liquid phase; and an aqueous liquid phase outlet to discharge the separated aqueous liquid phase from the separation vessel; a water analysis unit equipped with a plurality of sensors including at least two of a TDS sensor, a salinity sensor, a pH sensor, a conductivity sensor, a sodium concentration sensor, a chloride concentration sensor, a sulfate concentration sensor, a carbonate concentration sensor, and a nitrate concentration sensor; and one or more processors configured to: control to flow a diluted aqueous liquid phase sample into the water analysis unit, the diluted aqueous liquid phase sample including a measured amount of fresh water from a fresh water reservoir and a measured sample of the separated aqueous liquid phase from one of the plurality of separation vessels in which the separation operation has completed; control the plurality of sensors disposed in the water analysis unit to measure a set of sensor data corresponding to the diluted aqueous liquid phase sample; adjust the measured set of sensor data to account for the measured amount of fresh water in the diluted aqueous liquid phase sample, to obtain a set of sensor data corresponding to the separated aqueous liquid phase sample; transmit the set of sensor data corresponding to the separated aqueous liquid phase sample to a multiphase flow meter for calibration. In yet another embodiment, for each of the plurality of separation vessels, the multiphase fluid inlet and the demulsifier inlet are substantially at a top of the separation vessel, and the aqueous liquid phase outlet is substantially at a bottom of the separation vessel.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

Figure 1:
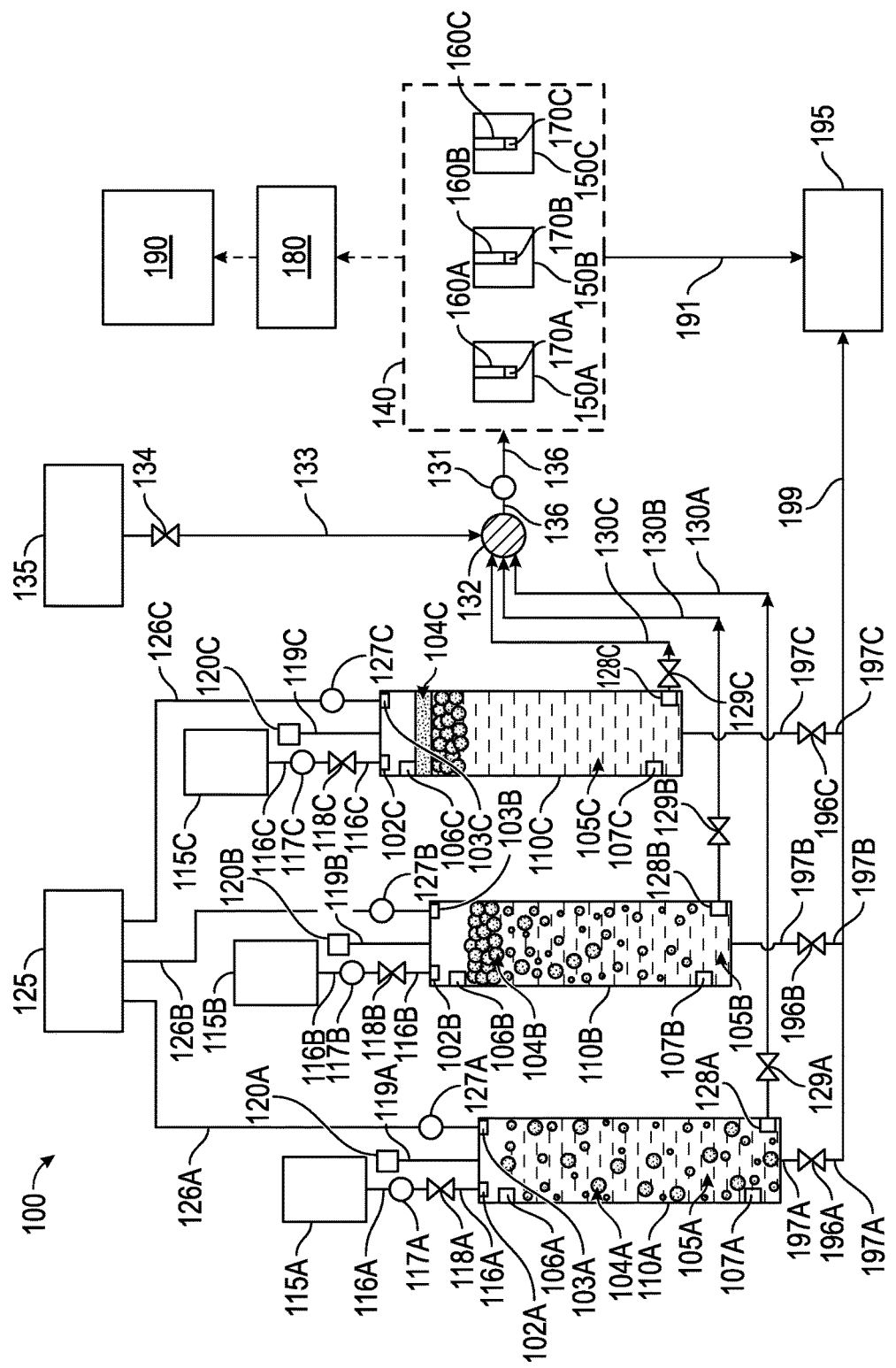
FIG. 1 is a schematic illustration of a system for separating and analyzing multiple aqueous liquid phase samples separated from respective discrete samples of multiphase fluids in accordance with one or more embodiments.

While certain embodiments will be described in connection with the illustrative embodiments shown herein, the subject matter of the present disclosure is not limited to those embodiments. On the contrary, all alternatives, modifications, and equivalents are included within the spirit and scope of the disclosed subject matter as defined by the claims. In the drawings, which are not to scale, the same reference numerals are used throughout the description and in the drawing figures for components and elements having the same structure.

DETAILED DESCRIPTION

In the following description, for purposes of explanation, numerous specific details are set forth in order to provide a thorough understanding of the inventive concept. In the interest of clarity, not all features of an actual implementation are described. Moreover, the language used in this disclosure has been principally selected for readability and instructional purposes, and may not have been selected to delineate or circumscribe the inventive subject matter, resort to the claims being necessary to determine such inventive subject matter. Reference in this disclosure to "one embodiment" or to "an embodiment" or "another embodiment" means that a particular feature, structure, or characteristic described in connection with the embodiment is included in at least one embodiment of the disclosed subject matter, and multiple references to "one embodiment" or "an embodiment" or "another embodiment" should not be understood as necessarily all referring to the same embodiment.

This disclosure pertains to a method and system for concurrently separating in multiple separation vessels, discrete samples of multiphase immiscible fluid mixtures (e.g., multiphase fluids) obtained from one or more wells, and measuring, in an analysis unit in fluid communication with the multiple separation vessels, geophysical properties of produced water samples separated from the discrete multiphase fluid samples in the multiple separation vessels, so as to expedite the measurements for the separated produced water samples by the analysis unit. When performing real-time measurements with the analysis unit of the separated produced water samples corresponding to one or more wells, timely availability of the separated produced water samples becomes a bottleneck, since the oil water separation in a separation vessel takes approximately two hours and fifteen minutes to achieve before a separated produced water sample can be flown out of the separation vessel and into the analysis unit for measurement. Since the measurement in the analysis unit takes less time (e.g., approximately 15 minutes), once the measurement at the analysis unit is completed for a first separated produced water sample, it becomes necessary to wait for a second separated produced water sample to become available, after the relatively longer oil water separation process in the separation vessel is completed.

In order to overcome the above problem, the present disclosure utilizes a system including a series of separation vessels and corresponding components (e.g., control valves, pump assemblies, level indicators, pipes, and the like), a water analysis unit (shared by the multiple separation vessels), and a control unit, where the oil water separation operation for multiple multiphase fluid samples from one or more wells can occur concurrently in the multiple separation vessels, and where the separated produced water sample from each separation vessel is allowed to flow into the shared water analysis unit for measurement, one water sample at-a-time. For example, ten (or more or less) separation vessels can be installed that are capable of selectively receiving multiphase fluid samples from one or more of a plurality of wells at a GOSP or at a well site.

Having an accurate view of the hydrocarbons produced from each of a plurality of wells enables operators to make decisions regarding the economic potential of each well, and of the oil field more generally. Advantageously, the method and system disclosed here are capable of providing near-instantaneous, real-time water sample measurements for each well that, when utilized to control, optimize or calibrate a corresponding MPFM, enables production engineers to obtain such an accurate view regarding the hydrocarbon production of each well. For example, wells producing a significant water cut can be identified, and isolated if necessary, so that resources are conserved. Because the system and method disclose herein can be automated, measurements can be carried out routinely in an unattended and uninterrupted manner with minimal labor costs and reduced potential for error. More specifically, data obtained using the system and method disclosed here can be used to calibrate, optimize, or control a MPFM, so that accurate flow rates of each phase of the multiphase fluid flowing out of each oil well can be measured. The measured data may also be used to assess the remaining productivity of the producing well. The system and method disclosed here thus enable real-time, faster, and more accurate measurement of data that provides the information necessary for the control and optimization of the oil field or the GOSPs output.

In operation, a control unit of the system is configured to control flow of a first multiphase fluid sample into a first separation vessel, where any residual oil is removed from the produced water, and further configured to control flow of a second multiphase fluid sample into a second separation vessel, where any residual oil is removed from the produced water. The control unit may further control to effect concurrent oil-water separation in the first and second separation vessels by adding respective predetermined measured amounts (and/or types) of demulsifier to the first and second multiphase fluid samples in the first and second separation vessels. The control unit may further be configured to cause a measured portion of the separated produced water of the first multiphase fluid from the first vessel to be diluted with fresh water and flow the diluted first sample to a water analysis unit, where certain geophysical or geochemical properties of the diluted water sample can be measured using sensors or probes. For example, geophysical or geochemical properties of the separated produced water the water analysis unit may be equipped to measure include conductivity, chloride content, sodium content, total dissolved solids (TDS), and the like. The control unit may further be configured to transmit data representing the measured properties of the separated produced water sample of the first multiphase fluid from the first vessel to an already existing MPFM associated with one or more wells from which the first multiphase fluid was obtained to calibrate, control, or optimize the flow rate measurements for each phase by the MPFM. Similarly, the control unit may further be configured to cause a measured portion of the separated produced water of the second multiphase fluid from the second vessel to be diluted with fresh water and flow the diluted second sample to the water analysis unit, where the geophysical or geochemical properties of the diluted water sample from the second vessel can be measured using the sensors or probes. Since, the oil water separation corresponding to the first and second multiphase fluids in the first and second vessels can occur concurrently, the separated produced water sample may be readily available when the measurement for the first sample from the first vessel is completed by the water analysis unit. As a result, the rate of measurements by the water analysis unit is increased. The control unit may further be configured to transmit data representing the measured properties of the separated produced water sample of the second multiphase fluid from the second vessel to the already existing MPFM associated with one or more wells from which the second multiphase fluid was obtained to calibrate, control, or optimize the flow rate measurements for each phase by the MPFM. The MPFM thus obtains the measurement data from a plurality of wells to accurately calculate a flow rate of oil flowing from the GOSP (or oil field) at any given time.

The system and method of the present disclosure is thus capable of automatically monitoring geophysical or geochemical properties of produced water by taking continuous reading of multiphase fluid samples from multiple wells at the GOSP or oil field. The system can easily take samples from multiple wells and then measure the properties of the separated produced water for each sample and feed the measurement directly into the MPFM. Utilization of multiple separation vessels allows monitoring of each well in approximately fifteen minutes instead of the conventional laboratory based system which takes approximately two to three days. The real-time water analysis unit may be installed proximal to the MPFM, the control unit can automatically divert samples from each well to the water analysis unit to analyze geochemical properties thereof, and the control unit can further automatically transmit the measurement data for each sample from the water analysis unit to the MPFM. Since the measurement data is automatically fed to the MPFM, manual sample collection and manual data entry into the MPFM is not required, and real-time measurement and monitoring for single or for multiple wells at the GOSP or at the oil field can be automatically performed without requiring constant human supervision or interruption.

FIG. 1 is a schematic illustration of system 100 for separating and analyzing multiple aqueous liquid phase samples separated from respective discrete samples of multiphase fluids, in accordance with one or more embodiments. System 100 represents the flow pattern and fill-up scheme of a multiphase fluid in each separation vessel, its separation and real-time measurement of geophysical or geochemical properties of an aqueous liquid phase (e.g., produced water) separated from the multiphase fluid. As shown in FIG. 1, system 100 includes a plurality of separation vessels (e.g., separation chambers) 110 (110A, 110B, and 110C) each having an inner chamber. In the embodiment shown in FIG. 1, system 100 is illustrated as including three separation vessels 110A, 110B, and 110C. However, this is not intended to be limiting. In other embodiments, system 100 may include two, four, or more than four separation vessels 110. The number of separation vessels can be extended to any reasonable number, based on the capability of water analysis unit 140 (described later) shared between the plurality of separation vessels 110, the capability of control unit 180 to handle the data output from water analysis unit 140 for each sample, the number of wells that are associated with system 100 and that are to be analyzed by water analysis unit 140 of system 100 (e.g., number of wells of a GOSP, number of wells at an oil filed, and the like), and the like. For example, system 100 may include ten (or more) separation vessels and corresponding components for each separation vessel, in a manner similar to that shown in FIG. 1.

Each separation vessel 110 may be manufactured from an at least partially translucent or transparent material such that the level of liquid inside vessel 110 can be determined by observation from outside separation vessel 110. For example, separation vessel 110 can be made of shatter-proof glass and can include markings for measuring the volume of liquid contained within. Each separation vessel 110 may be configured to receive and contain multiphase fluid from a selected well or group of wells from among a plurality of wells associated with system 100. The plurality of wells may belong to an oil field that is serviced by a GOSP to separate the multiphase fluid produced from each of the plurality of wells into constituent vapor and liquid components, and generate dry crude oil. For example, separation vessel 110 may be configured to receive and contain a discrete sample of multiphase fluid produced by a selected one of a plurality of wells associated with system 100. As another example, separation vessel 110 may be configured to receive and contain a discrete sample of multiphase fluid produced by a selected group of wells (e.g., 5 wells) from among a plurality of wells associated with system 100. As yet another example, two or more of the separation vessels 110A-110C may be configured to receive and contain discrete samples of multiphase fluid produced by a selected same well or a selected same group of wells from among the plurality of wells associated with system 100, to thereby continuously monitor and obtain measurement data in real-time, corresponding to the output from the selected same well or the selected same group of wells.

As shown in FIG. 1, system 100 further includes control unit 180 (e.g., programmable logic controller (PLC), central processing unit (CPU), graphics processing unit (GPU), system on a chip, application specific integrated circuit (ASIC), and the like) that may include predetermined control logic (implemented in hardware and/or software) and predetermined data to control and operate the various electronic components of system 100 shown in FIG. 1 to automate operations thereof. Although not specifically shown in FIG. 1, control unit 180 is communicatively coupled to the various electronic components of system 100 shown in FIG. 1 to communicate data and/or control signals with the components. Control unit 180 may be implemented on a computer system that is the same as or similar to computer system 300 described with regard to at least FIG. 3.

As shown in FIG. 1, separation vessels 110A-110C have multiphase fluid inlets 102A-102C respectively are in fluid communication with respective holding chambers 115A-115C (e.g., holding tank, high-pressure fluid line, and the like) via respective multiphase fluid couplings 116A-116C to receive discrete samples of multiphase fluids based on control operation of control unit 180. Each holding chamber 115 may be a high pressure, intermediate pressure or low pressure test trap for the multiphase fluid from a selected source. Alternately, in case system 100 is implemented at a GOSP, each holding chamber 115 may correspond to a high-pressure sample line where the multiphase liquid from the selected source (e.g., selected oil well or selected group of wells) may be flowing in at a high pressure. Each holding chamber 115 may be configured to selectively set at the selected source, one or more of the plurality of wells corresponding to the well site/oil field or to the GOSP.

Pump assemblies 117A-117C and inlet control valves 118A-118C may be disposed or installed on multiphase fluid couplings 116A-116C, respectively, to selectively start, stop, and control a flow rate of a stream of the multiphase fluid flowing through multiphase fluid couplings 116A-116C, based on control operations of control unit 180. Each pump assembly 117 may be driven by one or more electric motors. Alternately, pump assemblies 117A-117C may be driven by single electric motor or may be driven by two or more separate electric motors. Examples of electric motors system 100 may utilize include induction motors and/or permanent magnet motors. System 100 may further include one or more drives (e.g., variable frequency drives (VFDs; not shown) that monitor and control the electric motors, under control of control unit 180. The control drives, inlet control valves 118, and control unit 180 may together define a control system to automatically, selectively, and independently control (e.g., start, stop, change flow rate, and the like) a flow of the multiphase fluid for each separation vessel 110.

Further, as shown in FIG. 1, separation vessels 110A-110C may be equipped with first level indicators 106A-106C (e.g., level sensors) and second level indicators 107A-107C (e.g., level sensors), respectively. Each first level indicator 106 and each second level indicator 107 may be configured to detect a liquid level or fill level inside the inner chamber of the corresponding separation vessel 110. For example, second level indicator 107 may detect when the corresponding separation vessel 110 is empty (e.g., no multiphase fluid in vessel), and first level indicator 106 may detect when the corresponding separation vessel 110 is full (e.g., vessel full to capacity with the multiphase fluid). Additional level indicators (not shown) may be installed in each separation chamber 110 to detect intermediate fill levels (e.g., between full and empty) of vessel 110.

Control unit 180 may be configured to control operations of each pump assembly 117 and/or each control valve 118 based on sensor data indicating the fill level of the corresponding separation vessel 110 received from the corresponding first and second level indicators 106 and 107. For example, in response to receiving sensor data from first level indicator 106 indicating that the inner chamber of corresponding separation vessel 110 is full with a discrete sample of a received multiphase fluid, control unit 180 may be configured to control operations of corresponding pump assembly 117 and/or corresponding control valve 118 to stop flow of the multiphase fluid from corresponding holding chamber 115 into the separation vessel 110 via corresponding multiphase fluid coupling 116. Similarly, in response to receiving sensor data from second level indicator 107 indicating that the inner chamber of corresponding separation vessel 110 is empty, control unit 180 may be configured to control operations of corresponding pump assembly 117 and/or corresponding control valve 118 to start flow of a multiphase fluid from corresponding holding chamber 115 into separation vessel 110 via corresponding multiphase fluid coupling 116 to fill the inner chamber of separation vessel 110 with a discrete sample of the multiphase fluid. Each first level indicator 106 and each second level indicator 107 can be any device suitable for indicating the level of liquid held in the inner chamber of corresponding separation vessel 110, such as a sensor, a window, a float, and the like. Though FIG. 1 shows two level indicators (i.e., first level indicator 106 and second level indicator 107), a person of ordinary skill will appreciate that some embodiments can use a single level indicator, and others may use more than two level indicators.

The multiphase fluid, delivered via multiphase fluid couplings 116A-116C to separation vessels 110A-110C respectively, can be generally characterized as a fluid that includes a mixture of at least an aqueous liquid phase (e.g., produced water) and a nonpolar liquid phase (e.g., crude oil). Analyzing discrete samples contained in separation vessels 110A-110C allows greater control over the separation of aqueous liquid and nonpolar liquid phases than could be achieved using a continuous process. In some embodiments, the multiphase fluid can include aqueous liquid droplets dispersed in the nonpolar liquid phase, nonpolar liquid droplets dispersed in the aqueous liquid phase, or both. The multiphase fluid can include an emulsion of aqueous liquid droplets emulsified in the nonpolar liquid phase, nonpolar liquid phase droplets emulsified in the aqueous liquid phase, or both. The aqueous liquid phase can include produced water from a corresponding well or group of wells. The nonpolar liquid phase can include crude oil produced from a corresponding well or group of wells. The multiphase fluid can contain between about 5 and 95 vol % nonpolar liquid phase and between about 5 and 95 vol % aqueous liquid phase. If the multiphase fluid contains less than about 5 vol % aqueous liquid phase there may not be a sufficient amount of water in the discrete sample received and contained in each separation vessel 110 to separate it out and carry out analysis of geophysical properties thereof. According to at least one embodiment, the multiphase fluid can have a volume ratio of nonpolar liquid phase to aqueous liquid phase that is between about 99:1 and 30:70, alternately between about 95:5 and 40:60. In one or more embodiments, the multiphase fluid includes a gas phase. The gas phase can include gases produced from a corresponding well or group of wells, such as hydrocarbons, carbon oxides, hydrogen sulfide, mercaptans, and the like. The gas phase can be dissolved in the liquid phases of the multiphase fluid when it is introduced to a separation vessel 110.

As explained previously, the multiphase fluid in each separation vessel 110 can be a fluid obtained from a selected well or a selected group of wells. Alternately, the multiphase fluid in each separation vessel 110 may be a selected multiphase fluid that has at least partially been treated for separation of one or more of oil, water, and gas, after the extraction of the selected multiphase fluid from a well or a group of wells. That is, the multiphase fluid may be a selected multiphase fluid that has been processed at an upstream stage (upstream to separation vessel 110) to remove dissolved gases.

As the inner chamber of each separation vessel 110 is filled with the multiphase fluid, gases displaced by the multiphase fluid exit separation vessel 110 via corresponding gas flow line 119. Gas flow lines 119A-119C can also be used to vent gases that come out of the multiphase fluid during or after filling respective separation vessels 110A-110C and during the separation operation of the various liquid phases in the respective inner chambers. Gas flow meters 120A-120C may be disposed on gas flow lines 119A-119C respectively to measure the displaced or vented gas as it exits respective separation vessels 110A-110C. In some embodiments, control unit 180 may be communicatively coupled to flow meters 120A-120C to obtain a measurement of gas exiting respective separation vessels 110A-110C.

As shown in FIG. 1, system 100 further includes demulsifier source 125 that may be one or more containers or vessels (e.g., reservoirs, tanks, tubes, injectors, and the like) suitable for storing one or more types of demulsifiers. Separation vessels 110A-110C have demulsifier inlets 103A-103C, respectively, and demulsifier source 125 may be fluidly coupled to demulsifier inlets 103A-103C of separation vessels 110A-110C via respective demulsifier couplings 126A-126C to supply a measured (known or determined) amount and a determined type of demulsifier from demulsifier source 125 to respective separation vessels 110A-110C, based on the characteristics of the multiphase fluid contained in respective separation vessels 110A-110C, and under control of control unit 180. For example, control unit 180 may be configured to determine, based on predetermined characteristics of the discrete sample of the multiphase fluid in separation vessel 110A, the appropriate amount and type of demulsifier (from among a plurality of types of demulsifiers stored in source 125) to be used for introduction into the given separation vessel 110A and mixed with the multiphase fluid therein, so that an optimal or adequate level of separation between liquid phases including the aqueous liquid phase and the nonpolar liquid phase of the multiphase fluid in separation vessel 110A can be achieved in a predetermined period of time or under predetermined conditions.

Pump assemblies 127A-127C and additional sensors (e.g., flow meters; not shown) may be respectively disposed on demulsifier couplings 126A-126C to introduce the measured amount and the predetermined type of demulsifier from demulsifier source 125 into respective separation vessels 110A-110C, under control of control unit 180. Each pump assembly 127 may be driven by one or more electric motors. System 100 may further include one or more drives (e.g., VFDs; not shown) that monitor and control the electric motors under control of control unit 180. The control drives of pump assemblies 127A-127C, flow sensors, and control unit 180 may together define a control system for automatically introducing a measured amount and predetermined type of demulsifier from source 125 into each separation vessel 110 based on corresponding contained multiphase fluid.

The introduced measured amount and type of demulsifier from source 125 may be mixed with the multiphase fluid in a corresponding separation vessel 110 to obtain a demulsified multiphase fluid. In some embodiments, control unit 180 may be configured to mix the selected amount and type of demulsifier with the multiphase fluid before the mixture is introduced into separation vessel 110. In some embodiments, control unit 180 may actively mix the demulsifier with the multiphase fluid using a mixer (not shown) disposed inside the chamber of separation vessel 110.

The demulsifier can be any component, such as a surface-active agent, that facilitates the aggregation of dispersed droplets of the aqueous liquid phase or the nonpolar liquid phase. Control unit 180 may be configured to automatically select the type (and amount) of demulsifier based on the type of crude oil and the amount of produced water that is typically produced from the multiphase fluid inside separation vessel 110 where the demulsifier is to be added. Nonlimiting examples of suitable demulsifiers include: polyol block copolymers, alkoxylated alkyl phenol formaldehyde resins, epoxy resin alkoxylates, amine-initiated polyol block copolymers, modified silicone polyethers, silicone polyethers, or similar components, and combinations of the same. Such demulsifiers are available from The Dow Chemical Company, Inc. and Ecolab, Inc. The amount of demulsifier that control unit 180 is configured to use can be an amount sufficient to facilitate the aggregation of dispersed droplets of the aqueous liquid phase or nonpolar liquid phase such that the bulk aqueous liquid phase and nonpolar liquid phase are separated. However, excess demulsifier can slow separation of the multiphase fluid and produce very stable emulsions. According to at least one embodiment, the amount of demulsifier control unit 180 is configured to use can be enough to produce a concentration of between about 1 and 100 ppmv demulsifier, alternately between about 1 and 50 ppmv, alternately between about 1 and 25 ppmv, alternately between about 5 and 10 ppmv.

After mixing the demulsifier with the multiphase fluid in separation vessel 110, control unit 180 is configured to allow the demulsified multiphase fluid to settle inside separation vessel 110 for a predetermined period of time (that may depend on characteristics of the multiphase fluid being demulsified, and/or the amount/type of demulsifier used) or until a predetermined condition of the demulsified multiphase fluid is achieved, as determined based on data from one or more sensors (not shown). For example, the period of time can be predetermined to be between 1 minute and 24 hours, preferably between about 20 minutes and 12 hours, more preferably between about 1 and 5 hours. Also, the predetermined period of time may depend on the measured amount and type of demulsifier mixed into the multiphase fluid, and/or on the characteristics of the multiphase fluid in vessel 110. As a non-limiting example, the period of time can be predetermined to be approximately 2 hours and 15 minutes. In this case, control unit 180 may be configured so that after mixing the demulsifier with the multiphase fluid in separation vessel 110, control unit 180 may start a timer and may determine that the demulsified multiphase fluid has adequately separated into constituent liquid phases including a separated nonpolar liquid phase and a separated aqueous liquid phase after the predetermined period of time has elapsed (e.g., after 2 hours and 15 minutes). In another embodiment, separation vessel 110 may be equipped with one or more sensors (not shown) that may be configured to detect sensor data, and control unit 180 may be configured to receive the sensor data and make a determination based on the data as to whether the demulsified multiphase fluid has adequately separated into constituent liquid phases including a separated nonpolar liquid phase and a separated aqueous liquid phase.

For illustrative purposes only, FIG. 1 shows three different stages of separation between a nonpolar liquid phase and an aqueous liquid phase during the oil water separation operation in separation vessels 110A-110C filled with demulsified multiphase fluids. As illustrated in FIG. 1, separation vessel 110A shows an early stage of separation in which droplets of nonpolar liquid phase 104A are heavily emulsified in aqueous liquid phase 105A (e.g., countdown of the predetermined period of time has just started), separation vessel 110B shows an intermediate stage of separation in which dispersed droplets of nonpolar liquid phase 104B have begun to aggregate and accumulate on top of aqueous liquid phase 105B (e.g., countdown of the predetermined period of time has reached halfway), and separation vessel 110C shows an end stage of separation in which the demulsified multiphase fluid has adequately separated into liquid phases including a separated nonpolar liquid phase 104C and a separated aqueous liquid phase 105C (e.g., countdown of the predetermined period of time has completed).

Thus, as illustrated in FIG. 1, by implementing a plurality of separation vessels 110A-110C that can be continuously and selectively filled, emptied, and re-filled with demulsified multiphase fluids based on availability multiphase fluid samples from one or more wells whose water samples need to be analyzed, system 100 enables execution of the oil water separation operation concurrently in separation vessels 110A-110C. As a result, subsequent measurement performed by water analysis unit 140 can be performed in real-time, at a faster rate, and consecutively for the separated aqueous liquid phase samples acquired from respective separation vessel 110A-110C. That is, after completion of a measurement operation (e.g., analysis operation) by water analysis unit 140 for a first separated aqueous liquid phase sample from a first separation vessel, a next measurement operation by water analysis unit 140 for a second separated aqueous liquid phase sample from a second separation vessel can be performed without having to wait for the predetermined time period for the second separated aqueous liquid phase sample to become available.

As shown in FIG. 1, separation vessels 110A-110C further respectively include aqueous liquid phase outlets 128A-128C configured to draw a measured sample of the separate aqueous liquid phase after adequate separation thereof from the demulsified multiphase fluid (e.g., as shown in the case of vessel 110C). Each aqueous liquid phase outlet 128 may be located in a portion of corresponding separation vessel 110 where the aqueous liquid phase is likely to accumulate in a separated form. In many cases, the aqueous liquid phase will be denser than the nonpolar liquid phase and as a result, will settle beneath the nonpolar liquid phase (as evident from the separation in vessels 110B and 110C). Therefore, as shown in FIG. 1, aqueous liquid phase outlet 128 may be located in a lower portion of corresponding separation vessel 110. In at least one embodiment, aqueous liquid phase outlet 128 can be the opening of a tube, pipe, or conduit that is located in a portion of separation vessel 110 where the aqueous liquid phase is likely to accumulate after separating.

As shown in FIG. 1, aqueous liquid phase outlets 128A-128C may be in fluid communication with water analysis unit 140 via respective aqueous liquid phase couplings 130A-130C, junction 132 (e.g., manifold), and diluted sample coupling 136. Pump assembly 131 may be disposed on diluted sample coupling 136 and sample control valves 129A-129C may be disposed on aqueous liquid phase couplings 130A-130C, respectively, to selectively start, stop, and control a flow rate of streams of the aqueous liquid phase samples flowing through aqueous liquid phase couplings 130A-130C, under control of control unit 180. Pump assembly 131 may be driven by an electric motor. System 100 may further include one or more drives (e.g., VFDs; not shown) that monitor and control the electric motor of pump assembly 131 under control of control unit 180. The control drives, sample control valves 129A-129C, and control unit 180 may together define a control system for automatically controlling a flow of an aqueous liquid phase sample from separation vessel 110 to water analysis unit 140.

System 100 further includes fresh water reservoir (e.g., fresh water source) 135 which stores fresh water (e.g., deionized water). Fresh water reservoir 135 includes an outlet that is in fluid communication with water analysis unit 140 via fresh water coupling 133, junction 132, and diluted sample coupling 136. As shown in FIG. 1, fresh water control valve 134 may be disposed on fresh water coupling 133 to selectively start, stop, and control a flow rate of a stream of fresh water flowing through fresh water coupling 133, under control of control unit 180. The control drives of pump assembly 131, fresh water control valve 134, and control unit 180 may together define a control system for automatically controlling a flow of fresh water from fresh water reservoir 135 to water analysis unit 140.

During operation, when control unit 180 determines (e.g., based on passage of a corresponding predetermined period of time, or based on received sensor data) that the demulsified multiphase fluid in a particular separation vessel has adequately separated into liquid phases including the separated nonpolar liquid phase and the separated aqueous liquid phase (e.g., as shown in the case of separation vessel 110C with separated nonpolar liquid phase 104C and separated aqueous liquid phase 105C), and when control unit 180 further determines that water analysis unint 140 is ready to accept a next water sample for measurement, control unit 180 may be configured to control a corresponding sample control valve 129 and pump assembly 131 to draw a predetermined measured portion of the aqueous liquid phase (e.g., aqueous liquid phase sample; nondiluted aqueous liquid phase sample) from the separation vessel 110, via corresponding aqueous liquid phase coupling 130. Control unit 180 may further be configured to concurrently or separately control fresh water control valve 134 and pump assembly 131 to draw a predetermined amount of fresh water from reservoir 135 via fresh water coupling 133 to cause the stream of the aqueous liquid phase sample received via the corresponding aqueous liquid phase coupling 130 to mix with a stream of the predetermined amount of fresh water received via fresh water coupling 133, at junction 132, to generate diluted aqueous liquid phase sample. Control unit 180 may further be configured to convey the diluted aqueous liquid phase sample to water analysis unit 140. That is, control unit 180 may be configured to control the sample control valve 129, fresh water control valve 134, and pump assembly 131 to deliver and mix fresh water from fresh water reservoir 135 and the separated aqueous liquid phase sample from the separation vessel 110 at junction 132 to obtain a diluted aqueous liquid phase sample, and convey the diluted aqueous liquid phase sample to water analysis unit 140 via diluted sample coupling 136. Alternately, control unit 180 may be configured to control the sample control valve 129, fresh water control valve 134, and pump assembly 131, such that the separated aqueous liquid phase sample from the separation vessel 110 is conveyed to water analysis unit 140 via diluted sample coupling 136 separately from conveyance of the predetermined amount of fresh water from fresh water reservoir 135 to water analysis unit 140 via diluted sample coupling 136, so that the mixing and generation of the diluted aqueous liquid phase sample occurs (at least partially) inside (a flow cell of) water analysis unit 140.

Control unit 180 may control sample control valve 129 and pump assembly 131 to deliver a predetermined measured amount (i.e., mass, volume, or both) of the aqueous liquid phase as the aqueous liquid phase sample that is to be mixed with the fresh water prior to the measurement. For example, control unit 180 may utilize data from one or more sensors (e.g., flow meters; not shown) disposed on aqueous liquid phase coupling 130 to deliver the aqueous liquid phase sample having the measured amount. Similarly, control unit 180 may control fresh water control valve 134 and pump assembly 131 to deliver a predetermined measured amount (i.e., mass, volume, or both) of the fresh water as the predetermined amount of fresh water to dilute the aqueous liquid phase sample and generate the diluted aqueous liquid phase sample. For example, control unit 180 may utilize data from one or more sensors (e.g., flow meters; not shown) disposed on fresh water coupling 133 to deliver the fresh water having the measured amount. The amount of fresh water used to dilute the aqueous liquid phase sample can be predetermined based on preset criteria (e.g., type of multiphase fluid from which the aqueous liquid phase has been separated, application requirements, sensing capacity of sensors or probes 160A-160C, number of sensors or probes 160, size of flow cells 150 of water analysis unit 140, and the like). For example, the ratio of fresh water to aqueous liquid phase in the diluted aqueous liquid phase sample can be between about 50:1 and 1:1, preferably between about 30:1 and 1:1, more preferably between about 20:1 and 5:1.

System 100 further includes water analysis unit 140 which comprises one or more sensors 160A-160C for measuring one or more physical or chemical properties of the diluted aqueous liquid phase sample delivered thereto. As shown in FIG. 1, water analysis unit 140 is in fluid communication with the plurality of separation vessels 110A-110C, and is configured to receive an aqueous liquid phase sample from any separation vessel 110 under control of control unit 140. Water analysis unit 140 includes one or more sensors 160A-160C for measuring one or more properties of the diluted aqueous liquid phase sample including total dissolved solids (TDS), salinity, pH, conductivity, sodium concentration, chloride concentration, sulfate concentration, carbonate concentration, nitrate concentration, and the like. Each sensor installed in water analysis unit 140 for measuring one or more physical or chemical properties of the diluted aqueous liquid phase sample may be an ion-selective electrode. Diluting the aqueous liquid phase sample with fresh water ensures that the capacity of sensors 160A-160C is not overloaded, and increases the volume of relatively small samples so that they can be analyzed. This step can also reduce the corrosive potential of the aqueous liquid phase sample, allowing system 100 components to be manufactured from materials which would otherwise be unsuitable. Sensors 160A-160C may have a stainless-steel body, and sensing areas 170A-170C of respective electrodes 160A-160C may be covered with a layer of an ion-exchange polymer, which provides ruggedness and prevents fouling of sensing areas 170A-170C.

As illustrated in FIG. 1, water analysis unit 140 includes three flow cells: first flow cell 150A, second flow cell 150B, and third flow cell 150C. Each flow cell is equipped with a respective sensor (e.g., probe, electrode) 160A, 160B, and 160C for measuring geophysical or geochemical properties of the diluted aqueous liquid phase sample. Sensors 160A-160C have respective sensing areas 170A-170C. One or more of sensing areas 170A-170C may be covered with a layer of an ion-exchange polymer. Although FIG. 1 shows that each flow cell 150 is equipped with one corresponding sensor 160, this is not intended to be limiting. In some embodiments, each flow cell 150 may be equipped with multiple sensors. Also, the number of flow cells is not intended to be limiting. Some embodiments may include one or two or four or more flow cells, each with a corresponding number of (zero or more) sensors 160. Any suitable configuration of flow cell(s) and sensor(s) inside the flow cells can be deployed in water analysis unit 140 so long as desired geophysical or geochemical properties of the diluted aqueous liquid phase sample can be measured and recorded. Also, size, shape, and other characteristics of flow cell 150, electrode/sensor 160, and sensing area 170 are not intended to be limiting to what is shown in FIG. 1. Any suitable size, shape, and other characteristics of flow cell 150, electrode/sensor 160, and sensing area 170 may be employed so as to detect desired physical or chemical properties of the diluted aqueous liquid phase sample introduced in flow cell 150. Flow cells 150A-150C can be in fluid communication with each other so that they are coupled in series. Alternately, each flow cell 150 may be in fluid communication with diluted sample coupling 136 so that flow cells 150A-150C are coupled in parallel.

During operation, control unit 180 controls corresponding components to introduce the diluted aqueous liquid phase sample in each flow cell 150 to fill flow cell 150 with the diluted aqueous liquid phase sample such that it comes in predetermined contact with sensing area 170 of sensor 160. Control unit 180 may further be configured to control corresponding components so that the diluted aqueous liquid phase sample in each flow cell 150 remains in contact with corresponding sensor 160 for a predetermined period of time. The predetermined period of time may be preset (e.g., approximately 15 minutes), or may be determined based on predetermined logic of control unit 180. For example, the predetermined logic of control unit 180 may detect when the measurement or output of sensor 160 has stabilized or detect when a stable reading from sensor 160 has been obtained. And control unit 180 may be configured to maintain the diluted aqueous liquid phase sample in each flow cell 150 in contact with corresponding sensor 160 until the stable reading from sensor 160 has been detected. For example, the period of time can be between 30 seconds and 1 hour, preferably between about 1 minute and about 20 minutes, more preferably between about 5 minutes and 15 minutes. Once control unit 180 detects the stable reading or once the preset period of time has elapsed, control unit 180 stores in memory, a set of measurement data corresponding to the output of sensors 160A-160C as diluted aqueous liquid phase sample data. Control unit 180 may record the diluted aqueous liquid phase sample data in association with other relevant data such as data regarding the separation vessel 110 and/or the multiphase fluid from which the aqueous liquid phase sample was drawn, demulsifier data, data regarding the source of the corresponding aqueous liquid phase sample (e.g., well information) and the like.

Control unit 180 may further be configured to calculate approximate corresponding values from the diluted aqueous liquid phase sample data for the nondiluted aqueous liquid phase sample by adjusting the diluted aqueous liquid phase sample data to account for the measured amount of dilution with fresh water. That is, control unit 180 may be configured to calculate and record in memory, a set of measurement data corresponding to the nondiluted aqueous liquid phase sample as the nondiluted aqueous liquid phase sample data, based on the set of measurement data corresponding to diluted aqueous liquid phase sample, and based on data regarding the ratio of fresh water to aqueous liquid phase in the diluted aqueous liquid phase sample. Control unit 180 can also be configured to adjust the calculated nondiluted aqueous liquid phase sample data to account for properties of the fresh water. For example, if the property to be approximated is the concentration of a solute, the processing unit 180 can be configured to adjust the calculated nondiluted aqueous liquid phase sample data to account for a known preexisting concentration of the solute in the fresh water that is used to dilute the aqueous liquid phase sample.

As shown in FIG. 1, system 100 may further include MPFM 190 that is communicatively coupled to control unit 180. MPFM 190 may be used to measure the flow rate of oil and produced water of each of a plurality of wells or groups of wells at a GOSP or at a well site. Control unit 180 may be configured to transmit the calculated values for the nondiluted aqueous liquid phase sample data (e.g., (adjusted or recorded) set of measurement data corresponding to nondiluted aqueous liquid phase sample) to MPFM 190 to calibrate, optimize, or control MPFM 190, so that MPFM 190 can detect flow rates of each phase (e.g., oil and produced water) passing therethrough more accurately.

After the diluted aqueous liquid phase sample has been analyzed by sensors 160A-160C and corresponding diluted aqueous liquid phase sample data recorded, control unit 180 controls water analysis unit 140 to remove the diluted aqueous liquid phase sample from each flow cell 150A-150C of water analysis unit 140 via water analysis coupling 191 to drain equipment 195. Although not shown in FIG. 1, system 100 may include pump assemblies and/or control valves to remove the diluted aqueous liquid phase sample from each flow cell 150A-150C and flow the diluted aqueous liquid phase sample to drain equipment 195. After removal of the diluted aqueous liquid phase sample each flow cell 150A-150C, control unit 180 may further be configured to control pump assembly 131 and control valve 134 to flow fresh water from fresh water reservoir 135 into each flow cell 150A-150C to thereby flush (e.g., rinse) water analysis unit 140 and prepare it to receive subsequent samples.

Further, as shown in FIG. 1, separation vessels 110A-110C may be in fluid communication with drain equipment 195 via respective drain couplings 197A-197C and drain coupling 199 to drain the demulsified multiphase fluid in separation vessels 110A-110C, after the aqueous liquid phase sample has been extracted from the demulsified multiphase fluid via respective aqueous liquid phase couplings 130A-130C, or after the corresponding diluted (or nondiluted) aqueous liquid phase sample data has been recorded by control unit 180 in memory. Drain control valves 196A-196C may be respectively disposed on drain couplings 197A-197C to selectively start, stop, and control a flow rate of a stream of the demulsified and separated multiphase fluid being drained out of respective separation vessels 110A-110C under control of control unit 180. Drain control valves 196A-196C, and control unit 180 may together define a control system for automatically controlling draining of the demulsified and separated multiphase fluid out of respective separation vessels 110A-110C. Thus, after the diluted aqueous liquid phase sample has been analyzed by sensors 160A-160C and corresponding diluted aqueous liquid phase sample data recorded (or after the corresponding aqueous liquid phase sample has been drawn from separation vessel 110), control unit 180 may control drain control valve 196 to drain the demulsified and separated multiphase fluid from the corresponding separation vessel 110 via corresponding drain coupling 197 and drain coupling 199, to drain equipment 195, and prepare the emptied separation vessel 110 for a next sample of multiphase fluid. After emptying (e.g., based on second level indicator 107 indicating that the inner chamber of separation vessel 110 is empty) separation vessel 110 whose corresponding diluted aqueous liquid phase has been analyzed by water analysis unit 140 and corresponding nondiluted aqueous liquid phase sample data recorded in memory (or after the corresponding aqueous liquid phase sample has been drawn from separation vessel 110), control unit 180 may also be configured to flush (e.g., rinse) the inner chamber of the separation vessel 110 with fresh water from reservoir 135 in preparation for receiving a next discrete sample of multiphase fluid.

Meanwhile, since system 100 includes a plurality of separation vessels 110A-110C, where the oil water separation operation may be in progress in two or more vessels 110 concurrently, the separation operation in another one of the separation vessels 110A-110C (other than vessel 110 whose sample's at water analysis unit 140 just ended) may already have completed and corresponding separated aqueous liquid phase may be readily available for drawing of the next aqueous liquid phase sample for measurement by water analysis unit 140 without any wait period. For example, by the time the measurement operation for the aqueous liquid phase sample of separation vessel 110C in FIG. 1 is completed at water analysis unit 140, and corresponding nondiluted aqueous liquid phase sample data recorded in memory, the separation operation of the demulsified multiphase fluid in separation vessel 110B may have completed (e.g., elapse of the predetermined period of time). As a result, after completion of the analysis of the aqueous liquid phase sample drawn from separation vessel 110C (and after rinsing with fresh water), water analysis unit 140 can immediately start filling flow cells 150A-150C with the separated aqueous liquid phase sample drawn from separation vessel 110B, without wait. System 100 thus enables consecutive analysis and recording of data of diluted aqueous liquid phase samples obtained from different separation vessels 110A-110C, thereby increasing efficiency and reducing wait times where analysis unit 140 is waiting for a next sample from vessel 110 to become available. System 100 with multiple separation vessels 110A-110C thus enables continuous monitoring of oil wells at a GOSP or at an oil field.

The above process of system 100 thus repeats with each new discrete sample of the multiphase fluid introduced into separation vessels 110A-110C after analysis for a previous discrete sample of the multiphase fluid has been completed. The process can be automated by control unit 180 so that discrete samples of the multiphase fluid in multiple separation vessels 110A-110C are continuously measured in real-time, sets of measurement data recorded in memory, and the data transmitted to MPFM 190 for calibrating, optimizing, or controlling accuracy of data output from MPFM 190 with minimal or no supervision. The automation allows direct feeding of data to the MPFM to streamline and expedite the process of well monitoring, while reducing error. The system 100 can thus be used to analyze discrete multiphase fluid samples from individual wells, allowing less-productive wells to be identified and isolated.

Figure 2:
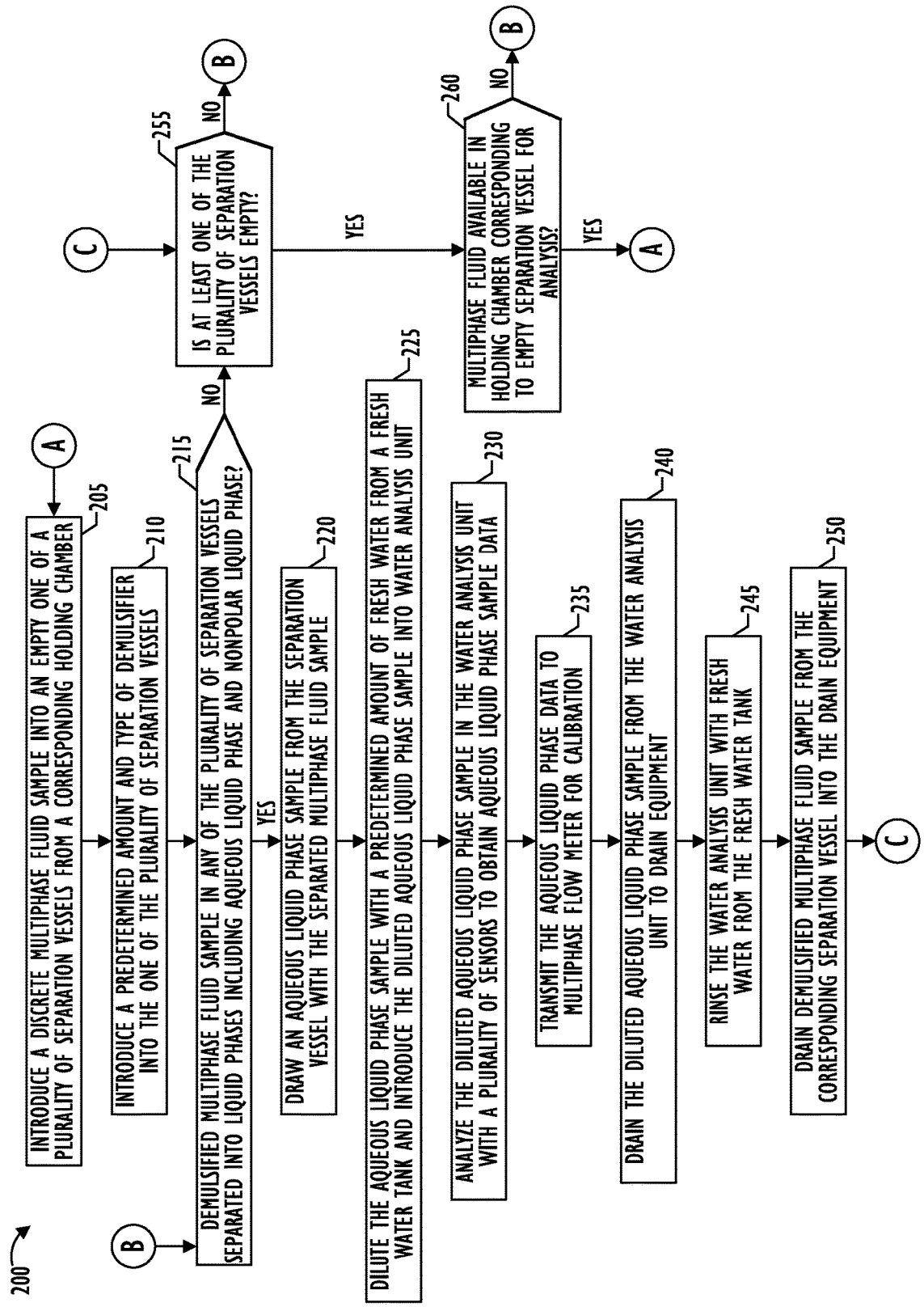
FIG. 2 is a flow chart that illustrates a method of operation of the system for separating and analyzing the multiple aqueous liquid phase samples separated from respective discrete samples of multiphase fluids in accordance with one or more embodiments.

FIG. 2 is a flow chart that illustrates method 200 of operation of the system illustrated in FIG. 1 in accordance with one or more embodiments. Method 200 begins at block 205 where a discrete sample of multiphase fluid is introduced into an empty one of a plurality of separation vessels from a corresponding holding chamber. At block 205, control unit 180 may control pump assembly 117 and inlet control valve 118 disposed on multiphase fluid coupling 116 of a separation vessel 110 determined to be in an empty state by control unit 180 (e.g., based on data received from corresponding first and second level indicators 106 and 107) to permit a discrete sample of multiphase fluid in a corresponding holding chamber 115 to flow into and fill the separation vessel 110. At block 205, control unit 180 may control to fill separation vessel 110 with the discrete sample of multiphase fluid so that data received from corresponding level indicators 106 and 107 indicate that separation vessel 110 is in a full state. The discrete sample may correspond to any selected well or group of wells whose produced water sample needs to be analyzed to measure properties thereof, and to calibrate the corresponding MPFM based on the measurement.

Method 200 then proceeds to block 210 where control unit 180 controls a corresponding pump assembly 127 to introduce a predetermined measured amount and type of demulsifier from demulsifier source 125 into the separation vessel filled with the multiphase fluid at block 205. At block 210, control unit 180 is configured to determine the measured amount and type of demulsifier to be introduced into the separation vessel based on predetermined data representing the type of crude oil and the amount of produced water that is typically produced from the multiphase fluid inside the separation vessel filled at block 205. Operations at block 205 and 210 thus effect separation of the discrete sample of multiphase fluid with the demulsifier added thereto into separate liquid phases including a separated aqueous liquid phase and a separated nonporous liquid phase. Operations corresponding to block 205 and 210 may be performed by control unit 180 multiple times to fill multiple (empty) separation vessels 110 with corresponding discrete samples of multiphase fluid and corresponding measured amounts and types of demulsifiers added thereto, based on availability of empty separation vessels and availability of discrete samples of multiphase fluids (from one or more wells) that need to be analyzed.

Method 200 then proceeds to block 215 where control unit 180 determines whether the discrete sample of multiphase fluid contained in any of the plurality of separation vessels has adequately separated into liquid phases including a separate aqueous liquid phase and a separate nonporous liquid phase. At block 215, control unit 180 may be configured to determine that adequate separation for a given discrete sample of multiphase fluid in a given one of the separation vessels 110 has been achieved (i.e., oil water separation operation completed) based on passage of a corresponding predetermined period of time since the introduction of the demulsifier into the given discrete sample, where the predetermined period of time may depend on the type and measured amount of demulsifier added to the given discrete sample, and/or depend on the type of crude oil and the amount of produced water that is typically produced from the multiphase fluid associated with the given discrete sample. For example, control unit 180 may determine that adequate separation for the given discrete sample in the given separation vessel 110 has been achieved when approximately 2 hours and 15 minutes have elapsed since introduction of the demulsifier into the given discrete sample. Alternately, or in addition, control unit 180 at block 215 may be configured to determine that the adequate separation for the given discrete sample has been achieved based on sensor data from one or more sensors (e.g., optical sensors, conductivity sensors, and the like) disposed in the given separation vessel indicating the adequate separation.

In response to control unit 180 determining that the given discrete sample in the given separation vessel as adequately separated into liquid phases including the separate aqueous liquid phase and the separate nonporous liquid phase (YES at block 215), method proceeds to block 220 where control unit 180 controls pump assembly 131 and corresponding sample control valve 129 to draw a measured sample of the separated aqueous liquid phase from the given separation vessel 110 for analysis. Method 200 then proceeds to block 225 where control unit 180 controls fresh water control valve 134 and pump assembly 131 to flow and mix a measured amount of fresh water from fresh water reservoir 135 with the aqueous liquid phase sample drawn at block 220 to generate a diluted aqueous liquid phase sample and flow the diluted aqueous liquid phase sample to each flow cell 150 of water analysis unit 140 for analysis. At blocks 220 and 225, control unit 180 may be configured draw a measured amount of the aqueous liquid phase as a nondiluted sample from the given separation vessel 110, and configured to draw a measured amount of fresh water from fresh water reservoir 135, using sensors (e.g., flow meters), so that the nondiluted aqueous liquid phase sample and the fresh water are mixed at a predetermined ratio (e.g., 5:1) to generate the diluted aqueous liquid phase sample. Mixing and generation of the diluted aqueous liquid phase sample may occur outside (e.g., at junction 132 of FIG. 1) and/or inside (e.g., first flow cell 150A) water analysis unit 140. For example, at blocks 220 and 225, control unit 180 may be configured so that first, the nondiluted aqueous liquid phase sample is flown into the flow cells 150A-150C of water analysis unit 140, and then, the measured amount of fresh water is flown into flow cells 150A-150C of the water analysis unit 140, so that the mixing and generation of the diluted aqueous liquid phase sample occurs at least partially inside water analysis unit 140.

Operations of blocks 220 and 225 are further illustrated by way of example, with reference to separation vessel 110C of FIG. 1. Since the discrete sample of multiphase fluid in separation vessel 110C has adequately separated into liquid phases including the separate aqueous liquid phase and the separate nonporous liquid phase (e.g., control unit determined that the corresponding predetermined period of time has elapsed since demulsifier was added to 110C), control unit 180 at block 220 operates pump assembly 131 and sample control valve 129C to draw a measured amount of separated aqueous liquid phase which has accumulated at the bottom of vessel 110C as the separated aqueous liquid phase sample, and concurrently or consecutively, control unit 180 at block 225 operates pump assembly 131 and fresh water control valve 134 to draw a measured amount of fresh water from reservoir 135, so that an aqueous liquid phase sample stream flowing from vessel 110C via couplings 130C and 136 combines and mixes with a fresh water stream flowing from reservoir 135 via couplings 133 and 136, to generate the diluted aqueous liquid phase sample, as it enters water analysis unit 140. As explained previously, water analysis unit 140 may include one or more flow cells 150, each cell including one or more sensors or probes 160 to measure one or more properties of the diluted aqueous liquid phase sample including total dissolved solids (TDS), salinity, pH, conductivity, sodium concentration, chloride concentration, sulfate concentration, carbonate concentration, nitrate concentration, and the like. At block 225, control unit 180 controls flow of the diluted aqueous liquid phase sample so that each flow cell 150 of water analysis unit 140 is filled with a portion of the diluted aqueous liquid phase sample and so that the portion of the diluted aqueous liquid phase sample in each flow cell comes in predetermined contact with sensing area 170 of sensor or probe 160 disposed in each flow cell 150.

Method 200 then proceeds to block 230 where the diluted aqueous liquid phase sample introduced in water analysis unit 140 is analyzed with sensors or probes 160 to obtain aqueous liquid phase sample data (e.g., set of measurement data corresponding to aqueous liquid phase sample of block 220). Continuing with the example of FIG. 1 where the aqueous liquid phase sample from separation vessel 110C is introduced into water analysis unit 140, and where water analysis unit 140 includes three flow cells 150A-150C respectively equipped with sensors 160A-160C, at block 230, control unit 180 controls to fill flow cell 150A with a first portion of the diluted aqueous liquid phase sample and maintain the first portion in predetermined contact with sensing area 170A of sensor 160A, fill flow cell 150B with a second portion of the diluted aqueous liquid phase sample and maintain the second portion in predetermined contact with sensing area 170B of sensor 160B, and fill flow cell 150C with a remaining portion of the diluted aqueous liquid phase sample and maintain the remaining portion in predetermined contact with sensing area 170C of sensor 160C. Further, control unit 180 may transmit control signals to sensors 160A-160C to cause sensors 160A-160C to continuously measure and transmit sensor data to control unit 180. Control unit 180 may be configured to maintain the predetermined contact in flow cells 150A-150C until the continuously received sensor data from sensors 160A-160C stabilizes, thereby indicating that a stable reading has been obtained.

The control unit 180 may be configured to record in memory the stabilized sensor data as diluted aqueous liquid phase sample data (e.g., set of measurement data corresponding to diluted aqueous liquid phase sample), and further configured to perform predetermined operations (e.g., account for the fresh water added to the aqueous liquid phase sample) on the diluted aqueous liquid phase sample data to obtain sensor data corresponding to the nondiluted aqueous liquid phase sample as it is obtained from separation vessel 110C (e.g., set of measurement data corresponding to nondiluted aqueous liquid phase sample). Control unit 180 may store the nondiluted aqueous liquid phase sample data in memory, along with corresponding data regarding the multiphase fluid in separation vessel 110C, and other corresponding data. At block 235, control unit 180 may transmit the (nondiluted) aqueous liquid phase sample data obtained at block 230 to MPFM 190 to calibrate, optimize, or control MPFM 190 so that MPFM 190 can detect flow rates of oil and produced water passing therethrough more accurately.

As a result, MPFM 190 is able to more accurately detect the constituent flow rates of various liquid phases (e.g., crude oil, produced water) of the multiphase fluid that was analyzed at block 230 and that is being produced from a corresponding well or group of wells whose output is flowing through a flowpath of MPFM 190.

Method 200 then proceeds to block 240 where control unit 180 operates one or more control valves and/or pump assemblies (not shown in FIG. 1) to drain the diluted aqueous liquid phase sample from each flow cell 150 of water analysis unit 140 and into drain equipment 195. At block 245, control unit 180 may control pump assembly 131 and control valve 134 to flow fresh water from fresh water reservoir 135 into each flow cell 150 of water analysis unit 140 to thereby flush the flow cells and prepare them for a next diluted sample. For example, after draining the sample at block 240, control unit 180 may cause fresh water to fill each flow cell 150 and further drain the fresh water from each flow cell of water analysis unit into drain equipment 195. This process may be performed one or more times, to prevent cross contamination between samples.

Next, at block 250, control unit 180 controls drain control valve 196 of the corresponding separation vessel 110 to drain the demulsified multiphase fluid contained in the separation vessel 110 to drain equipment 195. Continuing with the above example of FIG. 1 where the aqueous liquid phase sample from separation vessel 110C is introduced into water analysis unit 140, control unit 180 at block 250 controls drain control valve 196C to be in an open position (and optionally, drive a pump assembly (not shown)) to drain the demulsified and separated multiphase fluid out of separation vessel 110C via drain coupling 197C and drain coupling 199, to drain equipment 195. At block 250, control unit 180 may continue to drain demulsified and separated multiphase fluid out of separation vessel 110C until sensor data received from second level indicator 107C indicates that separation vessel 110C is empty. Control unit 180 at block 250 may also perform operations to rinse empty separation vessel 110C with fresh water from reservoir 135 prior to selectively filling separation vessel 110C with another discrete sample of multiphase fluid to prevent cross contamination.

Method 200 next proceeds to block 255 where control unit 180 determines (e.g., based on sensor data from first and second level indicators 106A-106C and 107A-107C) whether one or more of the plurality of separation vessels 110 are empty to receive a new discrete sample of multiphase fluid for analysis. In response to determining that an empty separation vessel 110 is available (YES at block 255), method 200 proceeds to block 260 where control unit 180 determines whether a multiphase fluid is available in a corresponding holding chamber for analysis. Continuing with the above example of FIG. 1 where demulsified and separated multiphase fluid of separation vessel 110C is drained and separation vessel 110C is now empty, at block 255 control unit 180 determines that separation vessel 110C is empty and available, and at block 260 control unit 180 determines (e.g., based on sensor data) whether another multiphase fluid sample is available in corresponding holding chamber (tank or high-pressure line) 115C for analysis. In response to determining at the multiphase fluid is available in the corresponding holding chamber (YES at block 260), method 200 returns to block 205 where a discrete sample of the multiphase fluid available in the corresponding holding chamber is introduced into the empty separation vessel (identified at block 255), and steps 205-260 of method 200 are repeated.

On the other hand, in response to control unit 180 determining (e.g., based on sensor data) that an empty separation vessel 110 is not available (NO at block 255), or in response to control unit 180 determining (e.g., based on sensor data) at another multiphase fluid sample is not available in the holding chamber corresponding to the empty separation vessel (NO at block 260), method returns to block 215 to wait for control unit 180 to determine that the oil water separation operation in one of the plurality of separation vessels 110A-110C has completed, as explained previously. Further, in response to control unit 180 determining that the oil water separation operation has not completed for any separation vessel 110 (NO at block 215), method proceeds to block 255, and if control unit 180 further determines that no empty separation vessels are available (NO at block 255) or that no multiphase fluid is available for analysis in a corresponding holding chamber of an empty separation vessel (YES at block 255; and NO at block 260), control unit 180 waits for the oil water separation operation in one of the plurality of separation vessels 110A-110C to be completed.

Continuing with the above example of FIG. 1, after demulsified and separated multiphase fluid out of separation vessel 110C is drained and separation vessel 110C is now empty (or filled with a new discrete sample of multiphase fluid from corresponding holding chamber 115C and mixed with demulsifier), control unit 180 at block 215 may now determine that the oil water separation operation in separation vessel 110B has completed (e.g., due to passage of the corresponding predetermined period of time), and multiphase fluid in separation vessel 110B has separated into liquid phases including a separated aqueous liquid phase and a separated nonpolar liquid phase (YES at block 215). As a result, control unit 180 will immediately start operations correspond to subsequent blocks 220-260, and begin the analysis operation of the separated aqueous liquid phase in separation vessel 110B by operating pump assembly 131 and sample control valve 129B to draw a measured amount of separated aqueous liquid phase which has accumulated at the bottom of vessel 110B as the separated aqueous liquid phase sample, dilute the aqueous liquid phase sample from vessel 110B with fresh water, introduce the diluted aqueous liquid phase sample from vessel 110B into each flow cell of water analysis unit for analysis, and transmit (nondiluted) aqueous liquid phase sample data for aqueous liquid phase sample from vessel 110B to MPFM 190. As a result, MPFM 190 is able to more accurately detect the constituent flow rates of various liquid phases (e.g., crude oil, produced water) of the multiphase fluid flowing therethrough and corresponding to vessel 110B.

Thus, with system 100 and method 200 described above, the separation operation of respective demulsified multiphase fluids contained in the inner chambers of separation vessels 110A-110C can occur concurrently, such that the separation operation of the demulsified multiphase fluid in vessel 110B can continue concurrently while separation operation of the demulsified multiphase fluid in vessel 110C is ongoing and also while control unit 180 is performing the measurement operation of the separated aqueous liquid phase of separation vessel 110C by operating pump assembly 131 and sample control valve 129C to draw a measured amount of separated aqueous liquid phase which has accumulated at the bottom of vessel 110C as the separated aqueous liquid phase sample, dilute the aqueous liquid phase sample from vessel 110C with fresh water, introduce the diluted aqueous liquid phase sample from vessel 110C into each flow cell of water analysis unit for analysis, obtain measurement data from sensors 160, and transmit (nondiluted) aqueous liquid phase sample data for aqueous liquid phase sample from vessel 110C to MPFM 190. As a result, by the time the above analysis operation for aqueous liquid phase in separation vessel 110C is completed and the aqueous liquid phase sample data transmitted to the MPFM, separation operation of the demulsified multiphase fluid in vessel 110B may have already completed. Consequently, control unit 180 can immediate start the steps for performing the analysis and measurement operation for the aqueous liquid phase in separation vessel 110B.

In other words, by repeatedly performing the above steps of method 200, multiple discrete multiphase fluid samples in different separation vessels (and corresponding to one well, multiple wells, or multiple groups of wells) can be analyzed consecutively, and the sample tests in the water analysis unit can be carried out in real-time, at a faster rate than when a single separation vessel is used. For example, in case each separation operation in the separation vessel takes 2 hours and 15 minutes, and each measurement operation in the water analysis unit takes 15 minutes, it will be necessary to wait for around two hours between consecutive measurement operations, if when only a single separation vessel is employed. However, since the present disclosure employs multiple separation vessels, even if the separation operation in each separation vessel were to take 2 hours and 15 minutes, and the measurement operation for each sample in the water analysis unit were to take 15 minutes, water analysis unit need not wait for around 2 hours between measurement operations for discrete samples, since multiple produced water samples are undergoing the separation operation concurrently in the separation vessels.

As a result, produced water samples can be analyzed by the water analysis unit at a higher rate, and the idle time of the water analysis unit can be reduced. Also, the MPFM is capable of accepting the aqueous liquid phase sample data corresponding to multiple (e.g., five or more) multiphase fluid samples, and utilize the multiple sets of measurement data to optimize or calibrate its operations. If a single separation vessel is employed, the aqueous liquid phase sample data can be provided to the MPFM at a slower rate. However, by implementing separation vessels multiple sets of measurement data corresponding to one or more wells can be provided to calibrate the MPFM at a faster rate. The system and method thus allows more wells to be tested and the generated data can directly be fed into the MPFM, leading to better accuracy of the data coming out of the MPFM.

Figure 3:
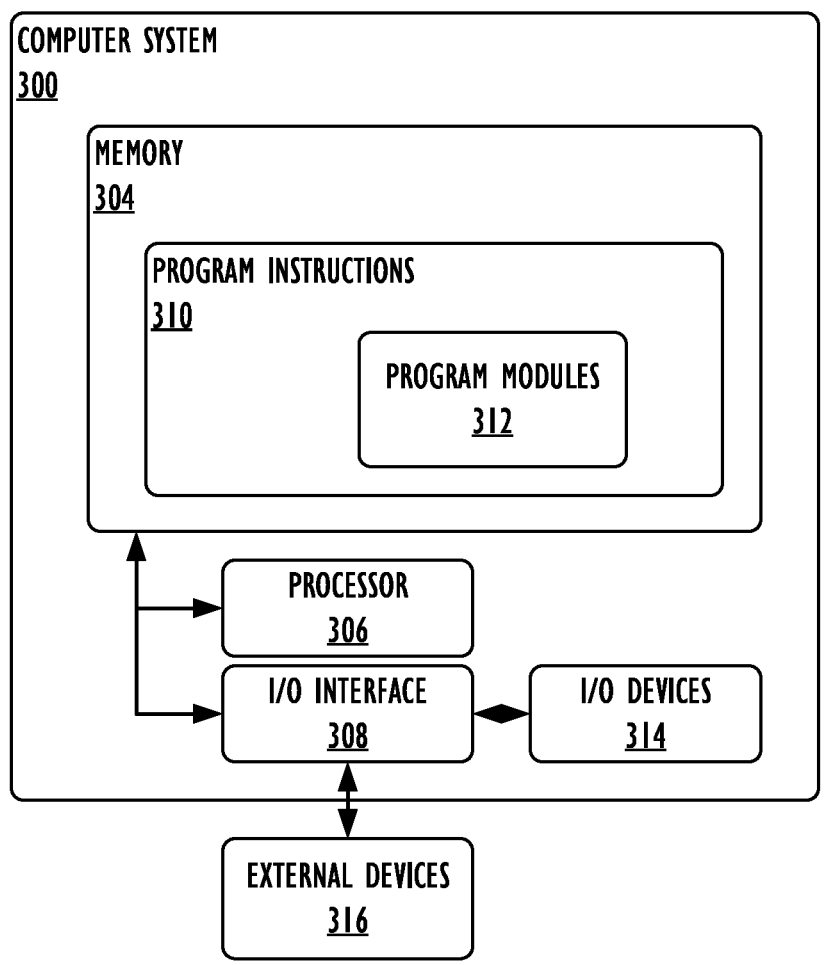
FIG. 3 is a functional block diagram of an exemplary computer system in accordance with one or more embodiments.

FIG. 3 is a functional block diagram of an exemplary computer system (or "system") 300 in accordance with one or more embodiments. In some embodiments, system 300 is a PLC, system on a chip, ASIC, and the like. System 300 may include memory 304, processor 306 and input/output (I/O) interface 308. Memory 304 may include non-volatile memory (e.g., flash memory, solid state memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), or bulk storage memory (e.g., CD-ROM or DVD-ROM, hard drives). Memory 304 may include a non-transitory computer-readable storage medium (e.g., non-transitory program storage device) having program instructions 310 stored thereon. Program instructions 310 may include program modules 312 that are executable by a computer processor (e.g., processor 306) to cause the functional operations described herein, such as those described with regard to control unit 180, MPFM 190, or method 200.

Processor 306 may be any suitable processor capable of executing program instructions. Processor 306 may include a central processing unit (CPU) that carries out program instructions (e.g., the program instructions of the program modules 312) to perform the arithmetical, logical, or input/output operations described. Processor 306 may include one or more processors. I/O interface 308 may provide an interface for communication with one or more I/O devices 314, such as a joystick, a computer mouse, a keyboard, or a display screen (for example, an electronic display for displaying a graphical user interface (GUI)). I/O devices 314 may include one or more of the user input devices. I/O devices 314 may be connected to I/O interface 308 by way of a wired connection (e.g., an Industrial Ethernet connection) or a wireless connection (e.g., a Wi-Fi connection). I/O interface 308 may provide an interface for communication with one or more external devices 316. In some embodiments, I/O interface 308 includes one or both of an antenna and a transceiver. In some embodiments, external devices 316 include any of the electronic components communicatively coupled to control unit 180 and that are described above in connection with FIGS. 1 and 2.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (e.g., meaning having the potential to), rather than the mandatory sense (e.g., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise.

Many other embodiments will be apparent to those of skill in the art upon reviewing the above description. The scope of the subject matter of the present disclosure therefore should be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system for separating and analyzing multiphase fluids, the system comprising:
   a plurality of separation vessels;
   a water analysis unit in fluid communication with each of the plurality of separation vessels, the water analysis unit including at least one sensor; and
   one or more processors operatively coupled to at least the sensor, the one or more processors configured to:
      draw a sample of a first aqueous liquid phase from a first one of the plurality of separation vessels in response to determining that a first separation operation in the first separation vessel has completed;
      obtain first aqueous liquid phase sample data by analyzing the first aqueous liquid phase sample with the at least one sensor in the water analysis unit;
      transmit the first aqueous liquid phase sample data to an external multiphase flow meter;
      draw a sample of a second aqueous liquid phase from a second one of the plurality of separation vessels in response to determining that a second separation operation in the second separation vessel has completed;
      obtain second aqueous liquid phase sample data by analyzing the second aqueous liquid phase sample with the at least one sensor in the water analysis unit; and
      transmit the second aqueous liquid phase sample data to the multiphase flow meter,
   wherein the first separation operation in the first separation vessel and the second separation operation in the second separation vessel are concurrent.

2. The system of claim 1, wherein the first separation operation is determined to be complete by the one or more processors when a first discrete sample of multiphase fluid contained in the first separation vessel has separated into liquid phases including the first aqueous liquid phase and a first nonpolar liquid phase, and the wherein the second separation operation is determined to be complete by the one or more processors when a second discrete sample of multiphase fluid contained in the second separation vessel has separated into liquid phases including the second aqueous liquid phase and a second nonpolar liquid phase.

3. The system of claim 2, wherein each of the plurality of separation vessels includes a multiphase fluid inlet, a demulsifier inlet, and at least one level sensor, and
   wherein the one or more processors are further operatively coupled to each level sensor, and are further configured to:
      introduce the first discrete sample of multiphase fluid into the first separation vessel via the multiphase fluid inlet thereof based on sensor data from the level sensor thereof;
      add a predetermined amount and type of demulsifier from a demulsifier source into the first separation vessel containing the first discrete sample of multiphase fluid via the demulsifier inlet thereof, wherein the first separation operation starts when the predetermined amount and type of demulsifier is added to the first separation vessel;
      introduce the second discrete sample of multiphase fluid into the second separation vessel via the multiphase fluid inlet thereof based on sensor data from the level sensor thereof; and
      add a predetermined amount and type of demulsifier from the demulsifier source into the second separation vessel containing the second discrete sample of multiphase fluid via the demulsifier inlet thereof, wherein the second separation operation starts when the predetermined amount and type of demulsifier is added to the second separation vessel.

4. The system of claim 3, wherein the one or more processors are further configured to:
   determine that the first separation operation is complete when a first predetermined period of time has elapsed since start of the first separation operation; and
   determine that the second separation operation is complete when a second predetermined period of time has elapsed since start of the second separation operation.

5. The system of claim 3, wherein the one or more processors are further configured to: determine the predetermined amount and type of demulsifier to be added to the first separation vessel based on at least one of a type of crude oil and an amount of produced water that is produced from the first discrete sample of multiphase fluid; and determine the predetermined amount and type of demulsifier to be added into the second separation vessel based on at least one of a type of crude oil and an amount of produced water that is produced from the second discrete sample of multiphase fluid.

6. The system of claim 3, further comprising: a plurality of gas flow lines that are in fluid communication with the plurality of separation vessels, respectively; and a plurality of flow meters respectively disposed on the plurality of gas flow lines and operatively coupled to the one or more processors, and wherein, for each separation vessel: the gas flow line vents a gas phase of the multiphase fluid contained therein, and one or more processors are further configured to control a flow meter from the plurality of flow meters to obtain measurement data of an amount of gas exiting the separation vessel.

7. The system of claim 1, wherein the one or more processors are further configured to: dilute the first aqueous liquid phase sample drawn from the first separation vessel with a predetermined amount of water from a water source to generate a first diluted aqueous liquid phase sample; measure first diluted aqueous liquid phase sample data by analyzing the first diluted aqueous liquid phase sample with the at least one sensor in the water analysis unit; obtain the first aqueous liquid phase sample data based on the measured first diluted aqueous liquid phase sample data and by accounting for the predetermined amount of water; dilute the second aqueous liquid phase sample drawn from the second separation vessel with the predetermined amount of water to generate a second diluted aqueous liquid phase sample; measure second diluted aqueous liquid phase sample data by analyzing the second diluted aqueous liquid phase sample with the at least one sensor in the water analysis unit; and obtain the second aqueous liquid phase sample data based on the measured second diluted aqueous liquid phase sample data and by accounting for the predetermined amount of water.

8. The system of claim 7, wherein the one or more processors are further configured to: drain the first diluted aqueous liquid phase sample from the water analysis unit; rinse one or more flow cells of the water analysis unit with water; and introduce the second diluted aqueous liquid phase sample in the water analysis unit to measure the second diluted aqueous liquid phase sample data after rinsing the one or more flow cells of the water analysis unit.

9. The system of claim 7, wherein the one or more processors are further configured to: maintain the first diluted aqueous liquid phase sample in predetermined contact with the at least one sensor in the water analysis unit until an output from the at least one sensor has stabilized; and measure the first diluted aqueous liquid phase sample data in response to determining that an output from the at least one sensor has stabilized.

10. The system of claim 9, wherein the one or more processors are further configured to determine that the output from the at least one sensor has stabilized based on passage of a predetermined period of time since start of the predetermined contact of the first diluted aqueous liquid phase sample with the at least one sensor in the water analysis unit.

11. The system of claim 7, wherein the one or more processors configured to draw the first aqueous liquid phase sample from the first separation vessel comprises the one or more processors configured to control a first sample control valve and a pump assembly to draw a predetermined amount of the first aqueous liquid phase from the first separation vessel as the first aqueous liquid phase sample, wherein the one or more processors configured to draw the second aqueous liquid phase sample from the second separation vessel comprises the one or more processors configured to control a second sample control valve and the pump assembly to draw a predetermined amount of the second aqueous liquid phase from the second separation vessel as the second aqueous liquid phase sample, and wherein the one or more processors configured to dilute each of the first and second aqueous liquid phase samples with the predetermined amount of water comprises the one or more processors configured to control a water control valve and the pump assembly to draw the predetermined amount of water from the water source.

12. The system of claim 1, wherein the at least one sensor includes a plurality of sensors to measure a plurality of properties of the first and second aqueous liquid phase samples, and wherein the plurality of sensors are selected from a group of sensors including a total dissolved solids (TDS) sensor, a salinity sensor, a pH sensor, a conductivity sensor, a sodium concentration sensor, a chloride concentration sensor, a sulfate concentration sensor, a carbonate concentration sensor, and a nitrate concentration sensor.

13. The system of claim 12, wherein each sensor has a sensing area that is covered with a layer of an ion-exchange polymer and that is to remain in predetermined contact with an aqueous liquid phase sample during the analysis.

14. A method for separating and analyzing multiphase fluids, the method comprising:
drawing a sample of a first aqueous liquid phase from a first one of a plurality of separation vessels in response to determining that a first separation operation in the first separation vessel has completed;
obtaining first aqueous liquid phase sample data by analyzing the first aqueous liquid phase sample with at least one sensor;
transmitting the first aqueous liquid phase sample data to an external multiphase flow meter;
drawing a sample of a second aqueous liquid phase from a second one of the plurality of separation vessels in response to determining that a second separation operation in the second separation vessel has completed;
obtaining second aqueous liquid phase sample data by analyzing the second aqueous liquid phase sample with the at least one sensor; and
transmitting the second aqueous liquid phase sample data to the multiphase flow meter,
wherein the first separation operation in the first separation vessel and the second separation operation in the second separation vessel are concurrent.

15. The method of claim 14, wherein the first separation operation is complete when a first discrete sample of multiphase fluid contained in the first separation vessel has separated into liquid phases including the first aqueous liquid phase and a first nonpolar liquid phase, and the wherein the second separation operation is complete when a second discrete sample of multiphase fluid contained in the second separation vessel has separated into liquid phases including the second aqueous liquid phase and a second nonpolar liquid phase.

16. The method of claim 15, wherein each of the plurality of separation vessels includes a multiphase fluid inlet, a demulsifier inlet, and at least one level sensor, and wherein the method further comprises:
introducing the first discrete sample of multiphase fluid into the first separation vessel via the multiphase fluid inlet thereof, based on sensor data from the level sensor thereof;
adding a predetermined amount and type of demulsifier from a demulsifier source into the first separation vessel containing the first discrete sample of multiphase fluid via the demulsifier inlet thereof, wherein the first separation operation starts when the predetermined amount and type of demulsifier is added to the first separation vessel;
introducing the second discrete sample of multiphase fluid into the second separation vessel via the multiphase fluid inlet thereof, based on sensor data from the level sensor thereof; and
adding a predetermined amount and type of demulsifier from the demulsifier source into the second separation vessel containing the second discrete sample of multiphase fluid via the demulsifier inlet thereof, wherein the second separation operation starts when the predetermined amount and type of demulsifier is added to the second separation vessel.

17. The method according to claim 16, further comprising:
determining that the first separation operation is complete when a first predetermined period of time has elapsed since start of the first separation operation; and
determining that the second separation operation is complete when a second predetermined period of time has elapsed since start of the second separation operation.

18. The method according to claim 16, further comprising: determining the predetermined amount and type of demulsifier to be added into the first separation vessel based on at least one of a type of crude oil and an amount of produced water that is produced from the first discrete sample of multiphase fluid; and determining the predetermined amount and type of demulsifier to be added into the second separation vessel based on at least one of a type of crude oil and an amount of produced water that is produced from the second discrete sample of multiphase fluid.

19. The method of claim 14, further comprising: diluting the first aqueous liquid phase sample drawn from the first separation vessel with a predetermined amount of water to generate a first diluted aqueous liquid phase sample; measuring first diluted aqueous liquid phase sample data by analyzing the first diluted aqueous liquid phase sample with the at least one sensor; obtaining the first aqueous liquid phase sample data based on the measured first diluted aqueous liquid phase sample data and by accounting for the predetermined amount of water; diluting the second aqueous liquid phase sample drawn from the second separation vessel with the predetermined amount of water to generate a second diluted aqueous liquid phase sample; measuring second diluted aqueous liquid phase sample data by analyzing the second diluted aqueous liquid phase sample with the at least one sensor; and obtaining the second aqueous liquid phase sample data based on the measured second diluted aqueous liquid phase sample data and by accounting for the predetermined amount of water.

20. The method according to claim 19, further comprising:
    draining the first diluted aqueous liquid phase sample;
    rinsing a flow cell corresponding to the at least one sensor with fresh water; and
    introducing the second diluted aqueous liquid phase sample to the flow cell to measure the second diluted aqueous liquid phase sample data after the rinsing.

21. The method according to claim 19, further comprising: maintaining the first diluted aqueous liquid phase sample in predetermined contact with the at least one sensor until an output from the at least one sensor has stabilized; and measuring the first diluted aqueous liquid phase sample data in response to determining that an output from the at least one sensor has stabilized.

22. The method according to claim 21, further comprising determining that the output from the at least one sensor has stabilized based on passage of a predetermined period of time since start of the predetermined contact of the first diluted aqueous liquid phase sample with the at least one sensor.

23. The method according to claim 19, wherein: the step of drawing the first aqueous liquid phase sample from the first separation vessel comprises controlling a first sample control valve and a pump assembly to draw a predetermined amount of the separated first aqueous liquid phase from the first separation vessel as the first aqueous liquid phase sample, the step of drawing the second aqueous liquid phase sample from the second separation vessel comprises controlling a second sample control valve and the pump assembly to draw a predetermined amount of the separated second aqueous liquid phase from the second separation vessel as the second aqueous liquid phase sample, and the steps of diluting each of the first and second aqueous liquid phase samples with the predetermined amount of water comprise controlling a water control valve and the pump assembly to add the predetermined amount of water to a respective aqueous liquid phase sample.

* * * * *